United States Patent
Seddon et al.

(10) Patent No.: US 11,529,454 B2
(45) Date of Patent: Dec. 20, 2022

(54) NEGATIVE PRESSURE WOUND THERAPY LEAK ALARM SYSTEM

(71) Applicant: KCI Licensing, Inc., San Antonio, TX (US)

(72) Inventors: James Seddon, Wimborne (GB); Benjamin A. Pratt, Poole (GB)

(73) Assignee: KCI Licensing, Inc., San Antonio, TX (US)

( * ) Notice: Subject to any disclaimer, the term of this patent is extended or adjusted under 35 U.S.C. 154(b) by 141 days.

(21) Appl. No.: 16/796,434

(22) Filed: Feb. 20, 2020

(65) Prior Publication Data

US 2020/0276367 A1 Sep. 3, 2020

Related U.S. Application Data

(60) Provisional application No. 62/812,088, filed on Feb. 28, 2019.

(51) Int. Cl.
*A61M 1/00* (2006.01)

(52) U.S. Cl.
CPC ........... *A61M 1/90* (2021.05); *A61M 2205/15* (2013.01); *A61M 2205/18* (2013.01);
(Continued)

(58) Field of Classification Search
CPC .......... A61M 2205/15; A61M 2205/18; A61M 2205/3306; A61M 2205/3327;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Andrew J Mensh

(57) ABSTRACT

One implementation of the present disclosure is a method for dynamically controlling an alarm of a negative pressure wound therapy (NPWT) device, according to some embodiments. In some embodiments, the method includes initiating NPWT, comparing an initial pump duty to a threshold value to determine a dressing application quality, monitoring a leakage rate of the NPWT, setting a leak threshold value based on the dressing application quality, determining leakage event occurrences in response to the leakage rate exceeding the leak threshold value at multiple times, adjusting the leak threshold value based on at least one of a number of the leakage events over the time period, a time duration between sequentially occurring leakage events of the leakage events, and the dressing application quality, and causing a user interface device to display a leak alert in response to the leakage rate exceeding the adjusted leak threshold value.

11 Claims, 9 Drawing Sheets

(52) U.S. Cl.
CPC ............... *A61M 2205/3306* (2013.01); *A61M 2205/3327* (2013.01); *A61M 2205/505* (2013.01); *A61M 2205/8212* (2013.01)

(58) Field of Classification Search
CPC .... A61M 2205/505; A61M 2205/8212; A61M 1/73; A61M 1/74; A61M 1/75; A61M 1/90
USPC ........................................................ 604/318
See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A * | 12/1987 | McNeil ................... | A61M 1/74 604/67 |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,734,425 B2 * | 5/2014 | Nicolini ................... | A61M 1/75 604/543 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2013/0110058 A1 | 5/2013 | Adie et al. | |
| 2013/0304006 A1 * | 11/2013 | Toth ...................... | A61B 5/14557 604/319 |
| 2017/0165405 A1 * | 6/2017 | Muser ..................... | A61M 1/90 |
| 2018/0185556 A1 * | 7/2018 | Askem .................... | A61M 1/90 |
| 2018/0250452 A1 * | 9/2018 | Locke ..................... | A61M 1/90 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

(56) References Cited

FOREIGN PATENT DOCUMENTS

| WO | WO-2013/015827 A2 | 1/2013 |
| WO | WO-2016/103031 A1 | 6/2016 |
| WO | WO-2018/041854 A1 | 3/2018 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al.; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion in International Application No. PCT/US2020/019051, dated May 28, 2020.

* cited by examiner

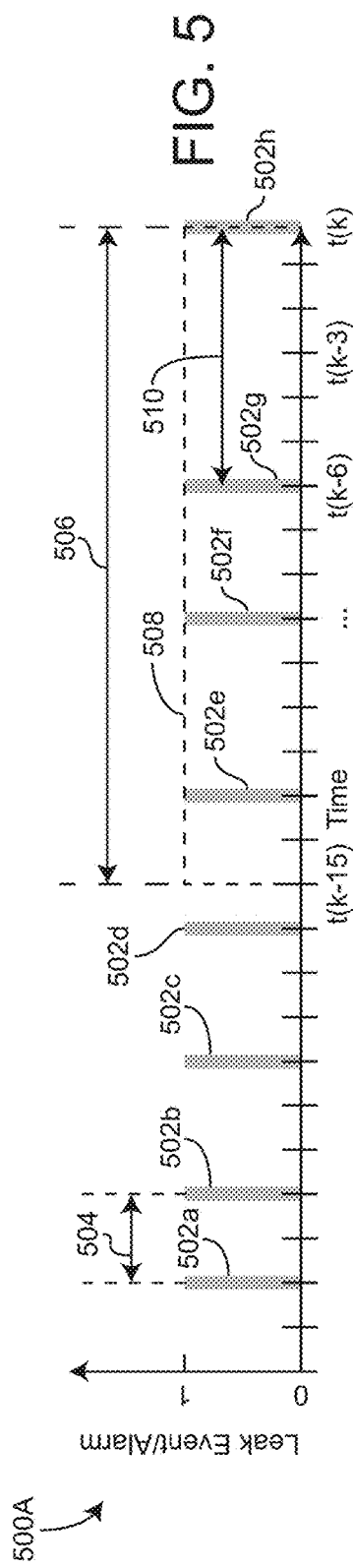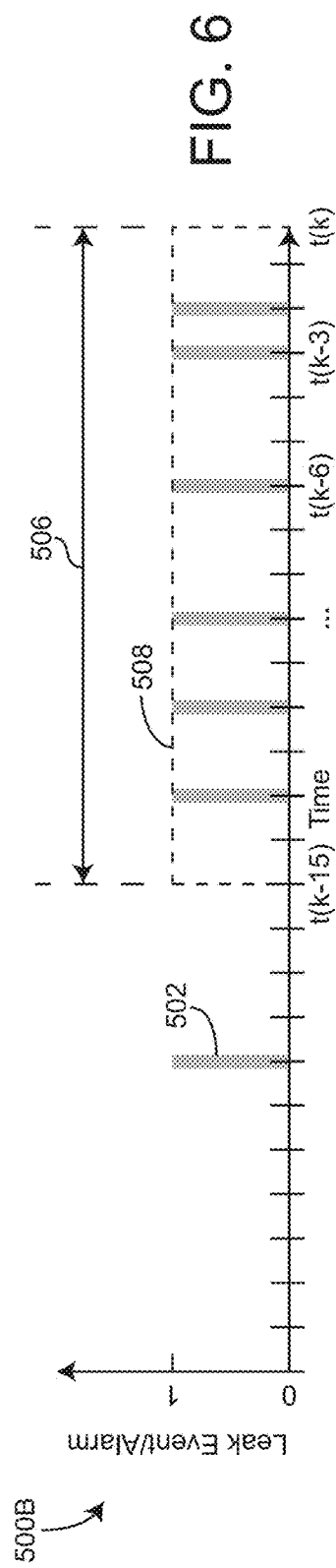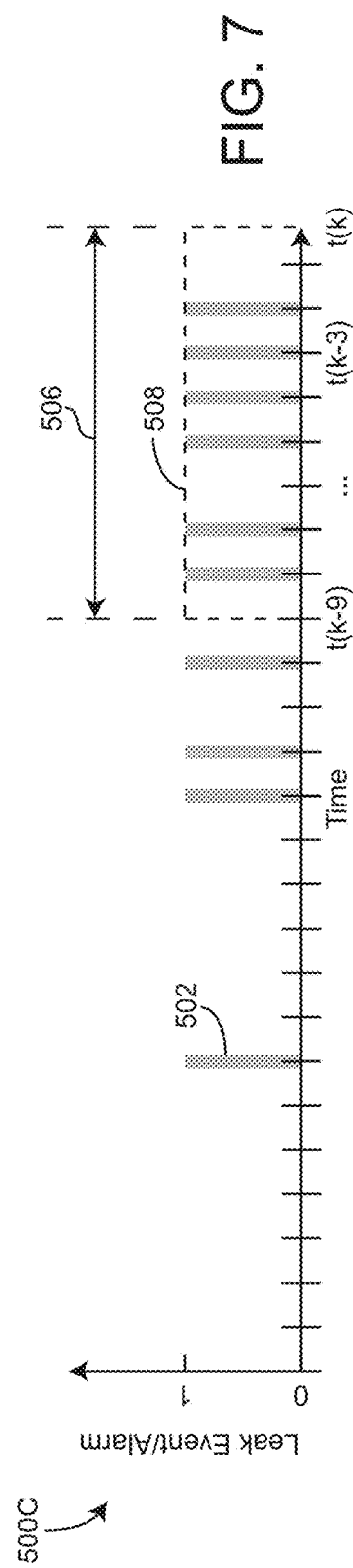

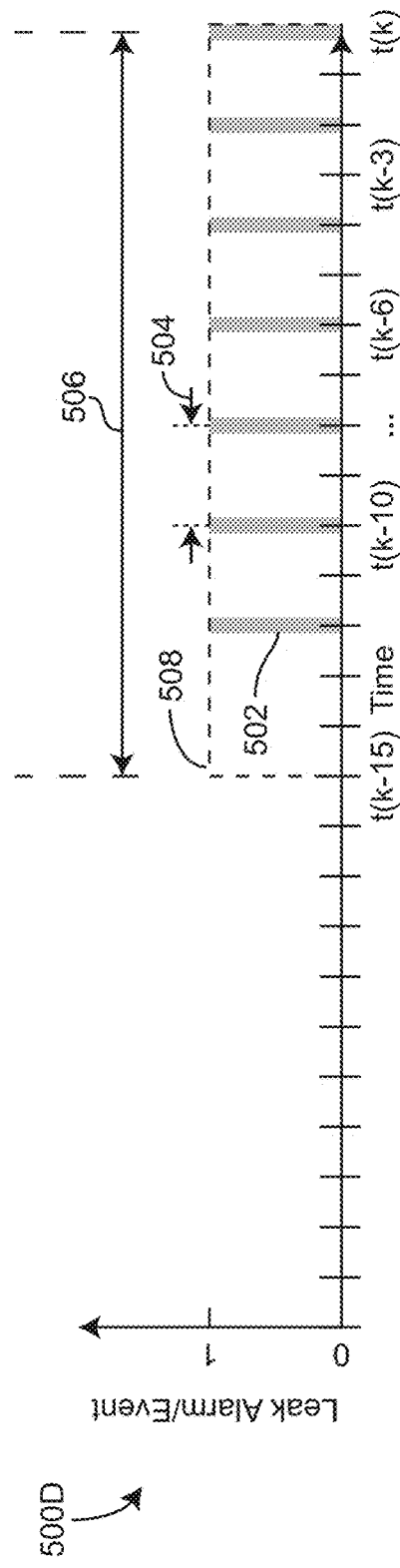
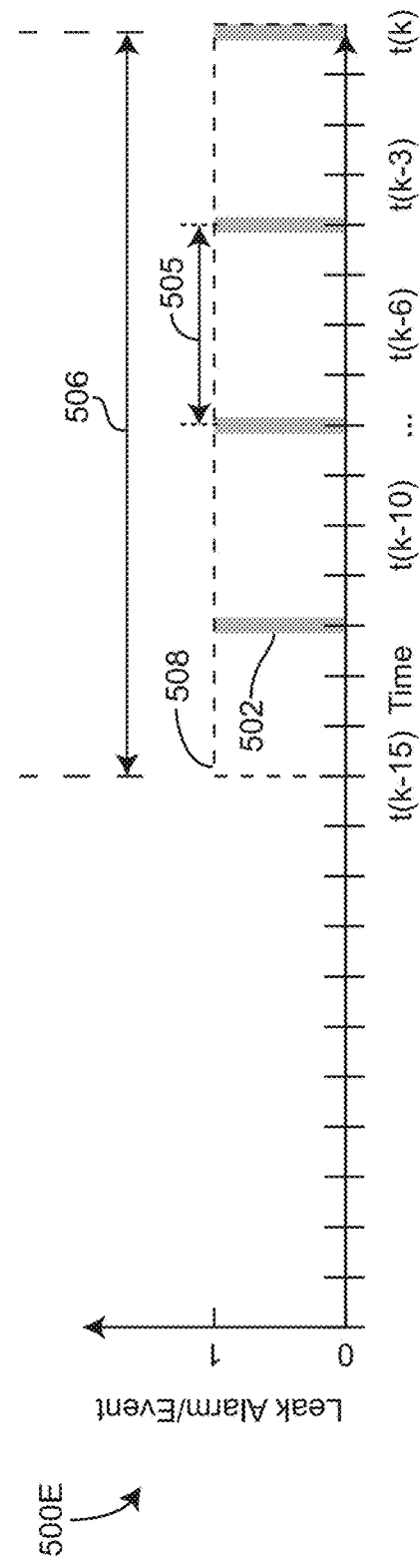

NEGATIVE PRESSURE WOUND THERAPY LEAK ALARM SYSTEM

CROSS-REFERENCE TO RELATED APPLICATIONS

This application claims the benefit of priority to U.S. Provisional Application No. 62/812,088, filed on Feb. 28, 2019, which is incorporated herein by reference in its entirety.

BACKGROUND

The present disclosure relates generally to negative pressure wound therapy (NPWT) devices and more particularly control algorithms for NPWT devices. It would be desirable to provide a NPWT device which dynamically adjusts one or more criteria for leak alarms to reduce a frequency of alarms and tailor the leak alarms to the specific dressing application.

SUMMARY

One implementation of the present disclosure is a method for dynamically controlling an alarm of a negative pressure wound therapy (NPWT) device, according to some embodiments. In some embodiments, the method includes initiating NPWT, comparing an initial pump duty to a threshold value to determine a dressing application quality, monitoring a leakage rate of the NPWT, setting a leak threshold value based on the dressing application quality, determining leakage event occurrences in response to the leakage rate exceeding the leak threshold value at multiple times, adjusting the leak threshold value based on at least one of a number of the leakage events over the time period, a time duration between sequentially occurring leakage events of the leakage events, and the dressing application quality, and causing a user interface device to display a leak alert in response to the leakage rate exceeding the adjusted leak threshold value.

In some embodiments, initiating NPWT includes increasing a vacuum pressure to draw down and seal a dressing for NPWT.

In some embodiments, determining the dressing application quality includes characterizing the dressing application as a low leak rate application in response to the initial pump duty being less than the threshold value and characterizing the dressing application as a high leak rate application in response to the initial pump duty being greater than the threshold value.

In some embodiments, the method includes receiving signals from an accelerometer to detect motion of the NPWT device.

In some embodiments, the method includes adjusting the leak threshold value based on the detected motion of the NPWT device.

In some embodiments, the method includes receiving location information from at least one of a GPS and a user device and adjusting the leak threshold value based on the received location.

In some embodiments, the method includes receiving information from a light sensor. In some embodiments, the information from the light sensor indicates an intensity of light at the NPWT device. In some embodiments, the method includes adjusting the leak threshold value based on the indicated light intensity.

In some embodiments, the method includes receiving information regarding a state of charge or a remaining amount of energy of an energy storage device configured to provide the NPWT device with power, and adjusting the leak threshold value based on the information regarding the state of charge or the remaining amount of energy of the energy storage device.

In some embodiments, the method includes increasing an amount of time between sequentially occurring leak alerts based on at least one of the number of the plurality of leakage events over the time period, and the dressing application quality.

Another implementation of the present disclosure is a negative pressure wound therapy (NPWT) device for NPWT, according to some embodiments. In some embodiments, the NPWT device includes a pump configured to draw a negative pressure on a wound application for NPWT, and a controller. In some embodiments, the controller is configured to monitor a leak rate, compare an initial leak rate to an initial threshold value to determine a seal quality of the NPWT, compare the leak rate to a leak rate threshold value to determine a leakage event, dynamically adjust the leak rate threshold value based on any of a number of leakage events over a previous time period, a time duration between sequentially occurring leakage events, and the seal quality of the NPWT, compare the leak rate to the adjusted leak rate threshold value, and provide a leak alert via a user interface in response to the leak rate exceeding the adjusted leak rate threshold value.

In some embodiments, the NPWT device includes an accelerometer. In some embodiments, the accelerometer is configured to detect motion of the NPWT device and provide the controller with detection of the motion.

In some embodiments, the controller is configured to use the detection of the motion to adjust the leak rate threshold.

In some embodiments, the NPWT device further includes a GPS. In some embodiments, the GPS is configured to monitor a current location of the NPWT device, monitor a current direction of motion of the NPWT device, determine a proximity of the NPWT device to a known charging location, and provide the controller with the current location, current direction of motion, and proximity of the NPWT device to the known charging device.

In some embodiments, the controller is further configured to use at least one of the current location of the NPWT device, the current direction of motion of the NPWT device, and the proximity of the NPWT device to the known charging location to adjust the leak rate threshold value.

In some embodiments, the controller is further configured to use any of the current location of the NPWT device, the current direction of motion of the NPWT device, and the proximity of the NPWT device to the known charging location to determine if the NPWT device is moving towards the known charging location, and adjust at least one of a time duration between sequential leak alerts and the leak rate threshold value based on the determination that the NPWT device is moving towards the known charging location.

In some embodiments, the controller is further configured to determine an initial seal quality of the NPWT by comparing an initial pump duty cycle value to a pump duty cycle threshold value.

In some embodiments, the controller includes a wireless radio configured to communicably connect with a user device and receive a position of the NPWT device from the user device.

In some embodiments, the controller is configured to receive power from a power source, and determine at least one of a remaining amount of charge in the power source and a remaining amount of energy in the power source.

In some embodiments, the controller is configured to use at least one of the remaining amount of charge in the power source and the remaining amount of energy in the power source to adjust at least one of the leak rate threshold value and a time between leak alerts.

Another implementation of the present disclosure is a controller for providing leak alerts for a Negative Pressure Wound Therapy (NPWT) device, according to some embodiments. In some embodiments, the controller is configured to determine an initial seal quality by comparing an initial pump duty value to a pump duty threshold value, monitor a leak rate of a NPWT seal, determine leak events in response to the leak rate exceeding a predetermined leak rate threshold value at multiple times over a time period, determine a number of the leak events over the time period, provide an alert in response to the leak rate exceeding the predetermined leak rate threshold, and adjust at least one of the predetermined leak rate threshold value and a time between alerts based on at least one of the initial seal quality and the number of the leak events over the time period.

In some embodiments, the controller is further configured to adjust at least one of the leak rate threshold value and the time between alerts based on at least one of a location of the NPWT device, a detection of motion of the NPWT device, and an amount of remaining battery life of the NPWT device.

Another implementation of the present disclosure is a method for dynamically controlling an alarm of a negative pressure wound therapy (NPWT) device, according to some embodiments. In some embodiments, the method includes initiating NPWT, determining a dressing application quality by monitoring a pressure or flow rate after reaching a target pressure, monitoring a leakage rate of the NPWT, and setting a leak threshold value based on the dressing application quality. In some embodiments, the method further includes determining multiple leakage event occurrences in response to the leakage rate exceeding the leak threshold value at multiple times. In some embodiments, the method further includes adjusting the leak threshold value based on at least one of a number of the leakage events over the time period, a time duration between sequentially occurring leakage events of the plurality of leakage events, and the dressing application quality. In some embodiments, the method further includes causing a user interface device to display a leak alert in response to the leakage rate exceeding the adjusted leak threshold value.

Another implementation of the present disclosure is a method for dynamically controlling an alarm of a negative pressure wound therapy (NPWT) device, according to some embodiments. In some embodiments, the method includes initiating NPWT, comparing a target pressure or target flow rate to a sensed pressure or a sensed flow rate to determine a dressing application quality, monitoring a leakage rate of the NPWT, and setting a leak threshold value based on the dressing application quality. In some embodiments, the method further includes determining multiple leakage event occurrences in response to the leakage rate exceeding the leak threshold value at multiple times. In some embodiments, the method further includes adjusting the leak threshold value based on at least one of a number of the leakage events over the time period, a time duration between sequentially occurring leakage events of the plurality of leakage events, and the dressing application quality. In some embodiments, the method further includes causing a user interface device to display a leak alert in response to the leakage rate exceeding the adjusted leak threshold value.

BRIEF DESCRIPTION OF THE DRAWINGS

FIG. 5 is a graph of leak alarms over a time period, according to some embodiments.

FIG. 6 is a graph of leak alarms over a time period, according to some embodiments.

FIG. 7 is a graph of leak alarms over a time period, according to some embodiments.

FIG. 8 is a graph of leak alarms over a time period, according to some embodiments.

FIG. 9 is a graph of leak alarms over a time period, according to some embodiments.

DETAILED DESCRIPTION

Overview

Figure 1:
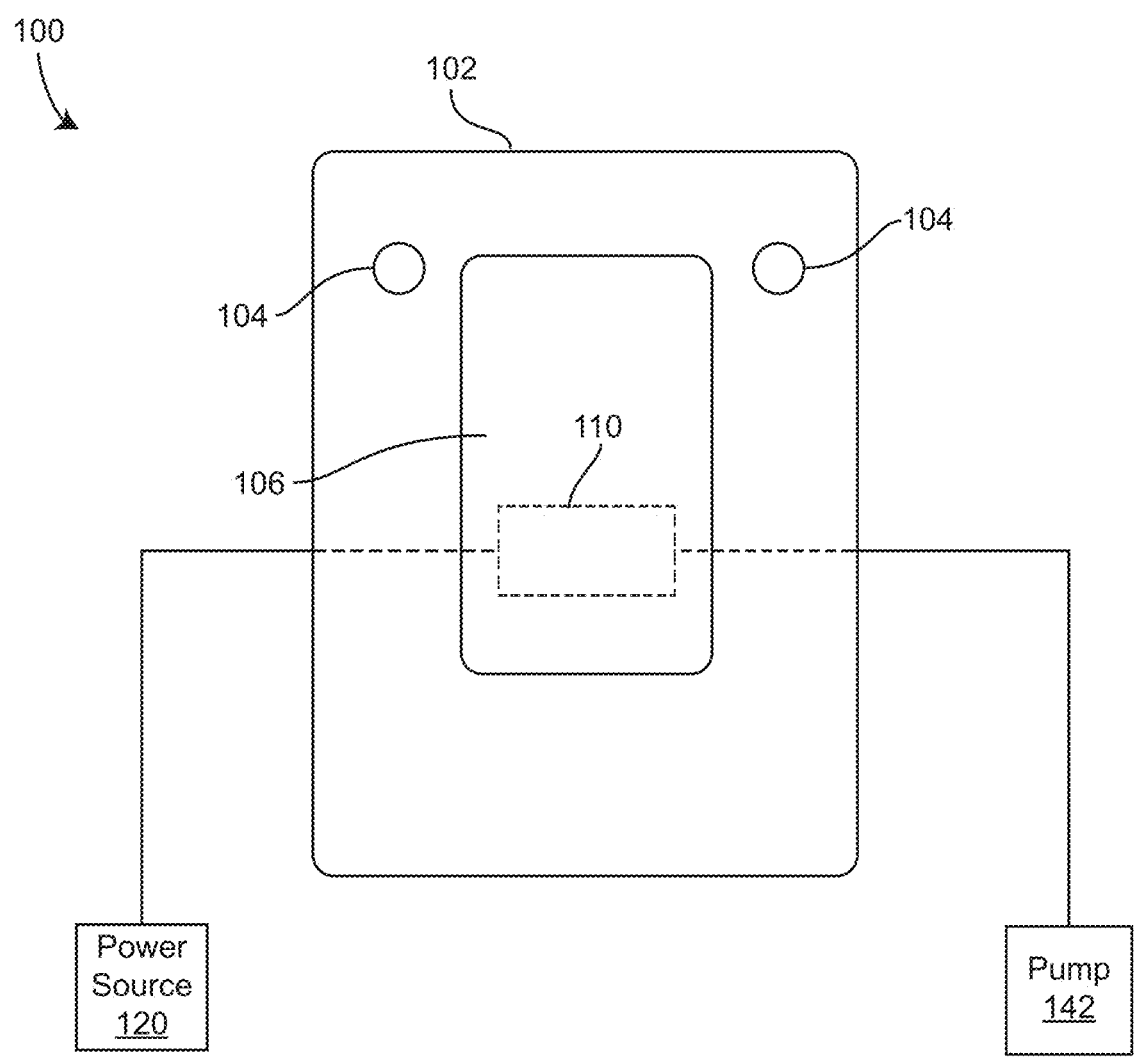
FIG. 1 is a front view of a NPWT device shown to include a user interface and a controller, according to some embodiments.

Referring generally to the FIGURES, an alarm system for a NPWT device is shown, according to some embodiments. The NPWT device may include a pump configured to draw a negative pressure to perform NPWT, and a controller configured to detect NPWT leakages and determine a leak alarm based on the detected NPWT leakages. The controller may be configured to dynamically adjust one or more leak alarm parameters to change an amount of leak alarms provided to a user/patient. In some embodiments, the controller uses initial wound application quality to initially set the one or more leak alarm parameters. For example, the NPWT may be characterized as a low leak application or a high leak application. The low leak application may indicate that an initial dressing application has a low leak rate and is at an easy to seal anatomical location. Therefore, for a low leak application, the controller may monitor a reliable seal throughout therapy. For a low leak application, the controller may lower a leak threshold value so that the user is alerted of potential seal failure before a traditional leak alarm would, thereby allowing the user to repair the dressing seal before major failure occurs. Alternatively, if the controller determines that the initial dressing application is a high leak application, due to the dressing application being in a hard-to-seal anatomical area, the controller may accept that the leak rate is high to begin with and set the leak threshold value higher so that the user is not continually provided with alarms. Throughout NPWT, the controller may adjust the one or more leak alarm parameters (e.g., leak threshold value) based on a rolling count of leak alarms over a previous time period and/or a time delay between subsequently occurring leak alarms. The leak alarm parameters may be adjusted to reduce customer annoyance and lack of compliance. In some embodiments, the controller only provides alerts if a certain amount of time has passed (e.g., the time delay) since a previous leak alarm. The controller and the alarm/alert system are capable of achieving the delay between subsequently occurring alarms due to initial tightening of the leak threshold value and increased capacity between the leak threshold value and a maximum leak threshold value.

In some embodiments, the controller receives input information from a variety of sensors (e.g., GPS, accelerometer, etc.) or from a power source. The controller may adjust the leak alarm parameters differently than described above based on whether or not the power source is a temporary power source (e.g., a battery) or if the power source is a main power source (e.g., a wall outlet). For example, if the power source is a battery, the controller may adjust the leak alarm parameters based on a remaining amount of battery capacity to reduce an amount of leak alarms to conserve battery capacity. Additionally, the controller may adjust the leak alarm parameters based on the input information from the variety of sensors.

If the controller or the alert system determines that the initial dressing application is reasonably poor (e.g., a high leak application), or that the dressing is in a hard-to-seal anatomical area, the controller may take alternative measures instead of repetitive alarming. The alternative measures may include, but are not limited to reducing therapy pressure, switching to Dynamic Pressure Control (DPC) or intermittent therapy, etc., to conserve battery life.

The alert system and the controller are configured to determine changes in leak rates that are out of the ordinary and unexpected rather than comparing the leak rates to a fixed threshold value, according to some embodiments. This facilitates tailoring the alert system to the specific dressing application which therefore allows the alarms to be tailored for each individual situation, according to some embodiments.

NPWT Device

Referring now to FIG. 1, a front view of a NPWT device 100 is shown, according to an exemplary embodiment. The NPWT device 100 includes a user interface 106, buttons 104, a housing 102, and a controller 110, according to some embodiments. In some embodiments, controller 110 is configured to control an operation of pump 142 to perform a NPWT. In some embodiments, NPWT device 100 is configured to control an operation of a V.A.C. VERAFLO™ Therapy, a PREVENA™ Therapy, an ABTHERA™ Open Abdomen Negative Pressure Therapy, or any other NPWT (e.g., controller 110 is configured to adjust an operation of pump 142 to perform any of the herein mentioned NPWT). In some embodiments, NPWT device 100 is configured to control an operation of any devices necessary to complete any of the herein mentioned NPWT (e.g., a pump, a vacuum system, an instillation system, etc.). In some embodiments, NPWT device 100 is a disposable NPWT device (dNPWT) and may have reusable/disposable parts. For example, NPWT device 100 may be relatively lightweight (e.g., less than 5 pounds), and may be portable, allowing a patient to transport NPWT device 100 while NPWT device 100 still performs NPWT, according to some embodiments. Since NPWT device 100 may be portable, NPWT device 100 may draw power from a portable power source (e.g., power source 120, a battery, etc.). The portable power source has a limited energy capacity, and therefore optimization of the portable power source is advantageous, since when the portable power source runs out of energy, NPWT can no longer be performed.

User interface 106 is configured to display any of an alarm/alert regarding at least one of a battery capacity of NPWT device 100, a leak, a pump duty cycle/pump duty value, etc., according to some embodiments. In some embodiments, user interface 106 is configured to provide any of a visual and an auditory alert. In some embodiments, user interface 106 allows a user to adjust an operation of the NPWT performed by NPWT device 100. For example, the user may provide a user input to controller 110 through user interface 106 to increase a pressure setpoint of pump 142, adjust a type of NPWT performed, adjust a parameter/operation of the performed NPWT, adjust a duration of the performed NPWT, pause the NPWT, start the NPWT, transition the NPWT device 100 into a "change" mode (e.g., so that wound dressings can be changed), etc. In some embodiments, user interface 106 is any of a resistive touch-screen interface, a surface acoustic wave touch-screen interface, a capacitive touch-screen interface, etc., configured to allow the user to control NPWT device 100. In some embodiments, user interface 106 is controlled by buttons 104. In some embodiments, buttons 104 are configured to control user interface 106 and/or to adjust an operation of the NPWT performed by NPWT device 100.

Figure 2:
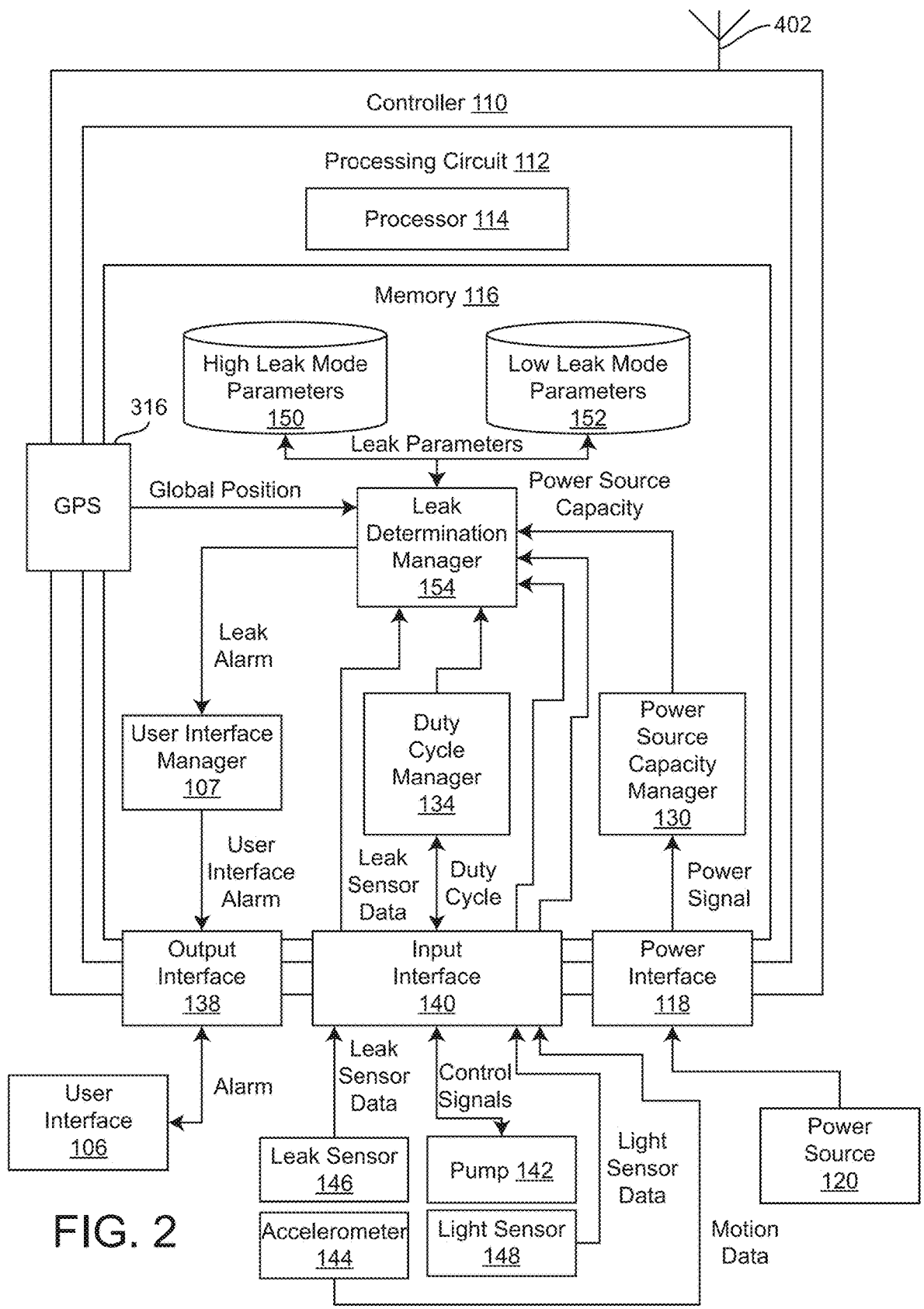
FIG. 2 is a block diagram of the controller of FIG. 1, shown to include a leak determination manager, according to some embodiments.

User interface 106 is also configured to display an operational status of the performed NPWT, according to some embodiments. For example, user interface 106 may display any of a patient name, a responsible caregiver's name, a type of NPWT currently being performed by NPWT device 100, a duration of NPWT, a time remaining in the current NPWT, a vacuum pressure of the NPWT, etc., or any other information relevant to the NPWT and/or operational status of NPWT device 100. For example, user interface 106 is configured to display a remaining battery life of a battery (e.g., power source 120 as shown in FIG. 2), and/or a duty cycle of the system configured to provide vacuum pressure to a wound (e.g., pump 142), according to some embodiments. In some embodiments, the remaining battery life of the battery is a remaining amount of energy in the battery. In some embodiments, the remaining battery life of the battery is a remaining amount of time which NPWT device 100 can sustain NPWT device at a current operational status.

Figure 4A:
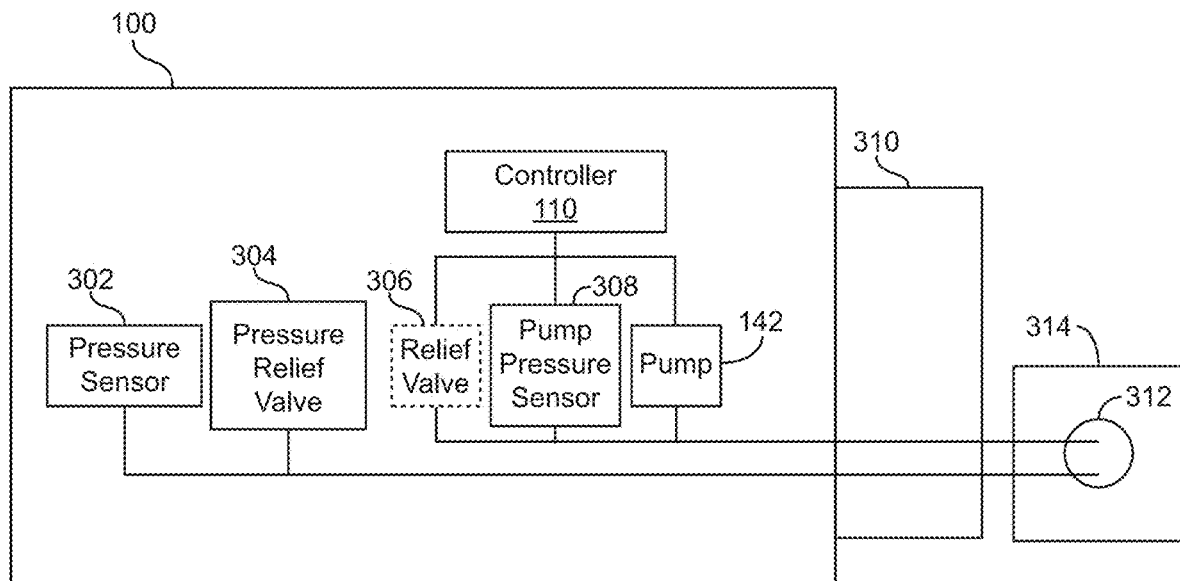
FIG. 4A is a block diagram of the NPWT device of FIG. 1, according to some embodiments.
Figure 4B:
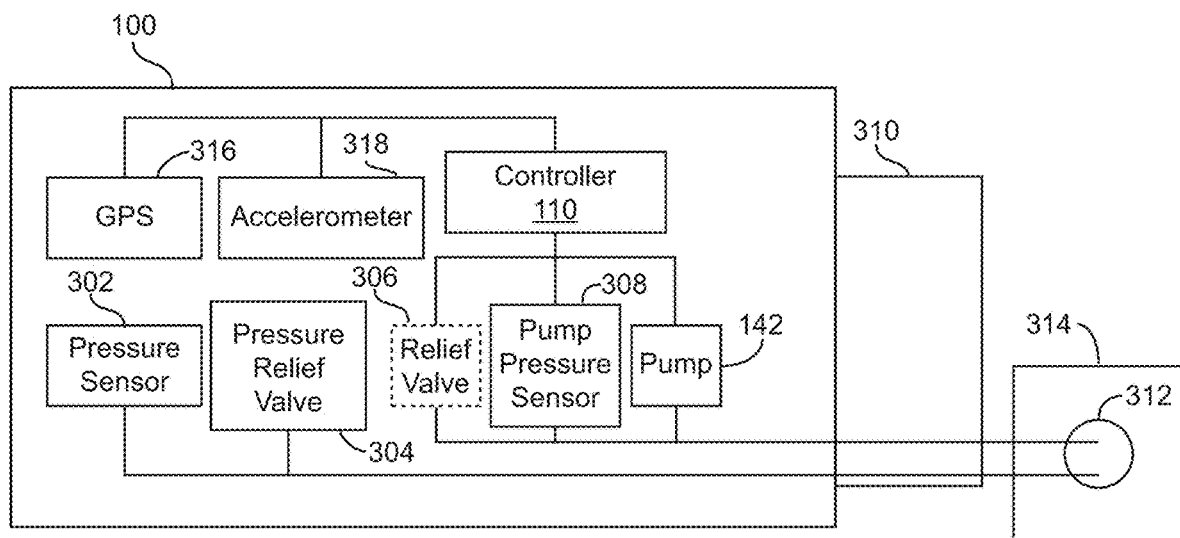
FIG. 4B is a block diagram of the NPWT device of FIG. 1, according to some embodiments.

Referring now to FIGS. 4A-4B, NPWT device 100 is shown in greater detail, according to some embodiments. In some embodiments, NPWT device 100 includes a pressure sensor 302, a pressure relief valve 304, a pump pressure sensor 308, and pump 142, as shown in FIG. 4A. In some embodiments, NPWT device 100 includes canister 310. In some embodiments, NPWT device 100 is configured to perform NPWT by producing a vacuum via pump 142 and pad/tubeset 312 for dressing 314. In some embodiments, controller 110 is configured to adjust an operation of pump 142 to perform the NPWT. In some embodiments, controller 110 receives pump pressure information from pump pressure sensor 308. In some embodiments, an optional relief valve 306 is installed to ensure that pump 142 does not produce an excessively high negative pressure. In some embodiments, pressure sensor 302 is a TRAC pressure sensor.

Referring now to FIG. 4B, NPWT device 100 is shown in greater detail, according to some embodiments. In some embodiments, NPWT device 100 as shown in FIG. 4B is the same as NPWT device 100 as shown in FIG. 4A, but includes GPS 316 and accelerometer 318. In some embodiments, controller 110 is configured to communicably connect with at least one of GPS 316 and accelerometer 318. In some embodiments, controller 110 receives information from GPS 316 regarding a current position, movement, proximity of NPWT device 100 to a known charging stations, etc., and uses any of the information from GPS 316 to adjust an operation of NPWT device 100 (e.g., to change leak alarm parameters to reduce alarms). In some embodiments, NPWT device 100 includes accelerometer 318. In some embodiments, NPWT device 100 is configured to receive acceleration signals from accelerometer 318 and use the acceleration signals to adjust an operation of NPWT device 100 (e.g., changing leak alarm parameters to reduce an amount of alarms).

In some embodiments, NPWT device 100 includes a light sensor. In some embodiments, the light sensor is a Charge-Coupled Device (CCD) configured to measure light intensity. In some embodiments the light sensor is a LCR sensor configured to measure light intensity. In some embodiments, light sensor is any device configured to measure a light intensity near or surrounding NPWT device 100. In some embodiments, NPWT device 100 includes a wireless radio (e.g., wireless radio 402 as shown in FIG. 2) configured to wirelessly communicably connect with a user device (e.g., a smart phone). In some embodiments, NPWT device 100 is configured to receive information regarding a global position of NPWT device 100, motion of NPWT device 100, proximity of NPWT device 100 to a charging location, etc., from the user device via the wireless radio. In some embodiments, the wireless radio is configured to communicably connect with the user device using any wireless communications protocol (e.g., Bluetooth, LoRa, Zigbee, etc.).

In some embodiments, NPWT device 100 is configured to characterize a quality of the NPWT application and whether a dressing associated with the NPWT application has a high or low initial leak rate. In some embodiments, NPWT device 100 characterizes the quality of the NPWT application based on any of mass air flow as measured by a sensor, or pump duty as provided to controller 110 by pump 142. In some embodiments, if the mass air flow and/or the pump duty are used to determine a leak rate of the NPWT. In some embodiments, if the leak rate of the NPWT device exceeds a leak threshold value, an alarm is triggered. In some embodiments, controller 110 examines a number of alarms over a previous time period, a time duration between alarms, and power source capacity to determine if the leak threshold value should be increased or decreased. In some embodiments, controller 110 determines if the leak threshold value should be increased or decreased based on information received from GPS 316, accelerometer 318, the light sensor, the user device, etc. The methods and functionality of controller 110 and how controller 110 adjusts the predetermined leak threshold value are described in greater detail below with reference to FIGS. 2, 3, and 5-11. Advantageously, adjusting the leak threshold value facilitates a dynamic alert system which can automatically adjust to provide a user with leak alarms/alerts based on situations, environment, motion, time of day, power source capacity, application quality, etc., according to some embodiments. This facilitates removing alarms which the user may consider annoying and disregard, according to some embodiments. Advantageously, adjusting the leak threshold value to change a quantity of leak alarms provided to the user reduces user annoyance, and provides a more efficient and accurate alert system to alert the user regarding high leaks, according to some embodiments.

Controller Configuration

Referring now to FIG. 2, a block diagram of controller 110 used in NPWT device 100 is shown, according to some embodiments. Controller 110 is configured to control an operation of pump 142 to perform the NWPT, according to some embodiments. In some embodiments, controller 110 is configured to dynamically adjust one or more parameters which cause an alarm/alert to be provided to a user regarding leakage. Controller 110 is shown to include a processing circuit, shown as processing circuit 112, according to some embodiments. Processing circuit 112 may be configured to perform some or all of the functionality of controller 110. Processing circuit 112 is shown to include a processor, shown as processor 114, according to some embodiments. Processor 114 may be a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Processor 114 may be a microprocessor, or, any conventional processor, controller, microcontroller, or state machine. Processor 114 also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. Processing circuit 112 also include memory, shown as memory 116. Memory 116 (e.g., memory, memory unit, storage device) may include one or more devices (e.g., RAM, ROM, Flash memory, hard disk storage) for storing data and/or computer code for completing or facilitating the various processes, layers and modules described in the present disclosure. Memory 116 may be or include volatile memory or non-volatile memory, and may include database components, object code components, script components, or any other type of information structure for supporting the various activities and information structures described herein. According to an exemplary embodiment, the memory 116 is communicably connected to the processor 114 via processing circuit 112 and includes computer code for executing (e.g., by the processing circuit or the processor) the one or more processes described herein.

Referring still to FIG. 2, controller 110 is shown to include a power interface, shown as power interface 118, according to an exemplary embodiment. Power interface 118 is configured to draw power supplied by a power source, shown as power source 120, to power controller 110, according to some embodiments. In some embodiments, power source 120 is any kind of permanent and/or temporary power source. In some embodiments, power source 120 is a battery. In some embodiments, power interface 118 is a connection port for a permanent power source (e.g., AC power and/or DC power) such as a wired 24 VAC connection. In other embodiments, power interface 118 includes both a port for permanent power and/or a power circuit configured to receive and transform power from power source 120. In some embodiments, power interface 118 is configured to receive power from both a permanent power source (e.g., an outlet) and a temporary power source (e.g., a battery). Power interface 118 may include any number of electrical components such as resistors, transistors, capacitors, inductors, diodes, transformers, transistors, switches, etc., necessary to receive, transform, and supply power to controller 110, according to some embodiments. In some embodiments, if power interface 118 is configured to receive power from a temporary power source (e.g., if power source 120 is a battery), power interface 118 may output power level data of power source 120 to processing circuit 112. The power level data may indicate an amount of energy remaining in power source 120 (e.g., a number of kW-hrs remaining in power source 120). In some embodiments, power source 120 is a replaceable power source (e.g., a battery). In some embodiments, power source 120 is one or more disposable batteries. For example, power source 120 is one or more disposable 12-volt batteries, according to some embodiments. In some embodiments, power source 120 is one or more rechargeable batteries. In some embodiments, power source 120 is configured to be temporarily disconnected from power interface 118 when the replaceable power source must be replaced (e.g., if power source 120 is one or more replaceable batteries, power source 120 may be disconnected when the battery level is low and the batteries must be replaced).

Referring still to FIG. 2, memory 116 is shown to include power source capacity manager 130, according to some embodiments. In some embodiments, power source capacity manager 130 is configured to receive information from power interface 118 regarding a remaining energy/charge of power source 120 or a type of power source 120 (e.g., a battery, MAINS power, etc.). In some embodiments, power source capacity manager 130 measures any of a supplied current from power source 120, a voltage from power source 120, and an amount of time power source 120 has provided power to controller 110. Power source capacity manager 130 may determine an amount of charge used over the amount of time power source 120 has provided power to controller 110, according to some embodiments. In some embodiments, power source capacity manager 130 determines an amount of energy used over the amount of time. For example, power source capacity manager 130 may determine an amount of charge used over a time period (e.g., using $Q=I*t$), and determine a remaining amount of charge of power source 120 based on a difference between a total charge capacity of power source 120 and the amount of charge used over the time period. In response to determining the amount of charge remaining in power source 120, power source capacity manager 130 may determine a remaining amount of energy in power source 120 (e.g., by $E=V*Q$). In some embodiments, power source capacity manager 130 uses supplied voltage from power source 120 to determine a remaining amount of energy in power source 120. Power source capacity manager 130 may receive an indication of remaining energy (or charge) in power source 120, or may determine remaining energy (or charge) in power source 120, according to some embodiments.

Referring still to FIG. 2, power source capacity manager 130 is shown providing leak determination manager 154 with an indication of an amount of energy remaining in power source 120 and/or a type of power source 120, according to some embodiments. For example, power source capacity manager 130 may provide leak determination manager 154 with any of a charge remaining in power source 120, an amount of energy (e.g., kW-hrs), a percent of remaining energy and/or charge in power source 120, and a type of power source 120 (e.g., battery or MAINS). Power source capacity manager 130 provides leak determination manager 154 with remaining energy level of power source 120 in a percentage (e.g., 50% charge remaining, 75% charge remaining, etc.), according to some embodiments. Leak determination manager 154 uses the indication of energy/charge remaining in power source 120 to determine leak alarm parameter changes, according to some embodiments. In some embodiments, leak determination manager 154 is configured to adjust a leak threshold value used to provide alerts based on the indication of energy/charge remaining in power source 120, described in greater detail below.

Referring still to FIG. 2, controller 110 is shown to include input interface 140 and output interface 138, according to some embodiments. Input interface 140 is configured to receive inputs from at least one of pump 142, user interface 106, leak sensor 146, accelerometer 144, light sensor 148, wireless radio 402, and GPS 316, according to some embodiments. In some embodiments, input interface 140 receives commands and/or requests from user interface 106. For example, controller 110 may receive a command from user interface 106 via input interface 140 to transition NPWT device 100 between various modes of operation, or to adjust an operational characteristic of the NPWT being performed by NPWT device 100 (e.g., increasing a pressure setpoint, increasing an amount of therapy time, etc.). Input interface 140 is also configured to receive information from pump 142 regarding an actual therapy pressure or a pump duty, according to some embodiments. Output interface 138 is configured to receive alarms, alerts, notifications, etc., from user interface manager 107 and provide user interface 106 with a command to alert the user (e.g., display a message, provide an aural alert, provide a visual alert, etc.).

Pump 142 is configured to provide the therapy pressure to a wound, with a seal being placed between the wound and vacuum tubes used to apply the therapy pressure (e.g., negative pressure) to the wound, according to some embodiments. The vacuum tubes, wound, and any other vacuum elements used to provide the therapy pressure to the wound may be referred to as the vacuum system, according to some embodiments. The seal between the wound and the vacuum tubes may sometimes leak, causing controller 110 to increase a duty cycle of pump 142 to achieve the therapy pressure setpoint (i.e., actual therapy pressure=setpoint therapy pressure). In order to overcome pressure losses due to the leakage, pump 142 must operate at a higher pump duty cycle. In this way, a leak in the vacuum system is positively correlated to the duty cycle required to achieve the therapy pressure setpoint. Therefore, an unusually high pump duty cycle to achieve the therapy pressure setpoint may indicate a leak in the vacuum system, according to some embodiments. In this way, leaks may be identified and alerts may be provided to the user through user interface 106, according to some embodiments. Additionally, the identification of leaks and the corresponding pump duty cycle may be used by leak determination manager 154 to determine changes to leak alarm parameters.

Referring still to FIG. 2, controller 110 is shown to include duty cycle manager 134, according to some embodiments. Duty cycle manager 134 is configured to monitor or control a current pump duty cycle of pump 142, according to some embodiments. In some embodiments, duty cycle manager 134 is configured to supply the monitored current pump duty cycle of pump 142 to leak determination manager 154. In some embodiments, duty cycle manager 134 stores historical information of pump duty cycles of pump 142 over a time period, and supplies this historical information to leak determination manager 154. For example, duty cycle manager 134 may identify and store a maximum pump duty cycle and provide the maximum pump duty cycle to leak determination manager 154, according to some embodiments. In some embodiments, duty cycle manager 134 may store a pump duty cycle threshold value and compare the monitored pump duty cycle value of pump 142 to the pump duty cycle threshold value. In some embodiments, the pump duty cycle threshold value is a predetermined value. In some embodiments, the pump duty cycle threshold value is determined based on at least one of a type of NPWT being performed (e.g., V.A.C. VERAFLO™ Therapy, PREVENA™ Therapy, ABTHERA™ Therapy, etc.) a type of NPWT device (e.g., various models of NPWT device 100), a type of pump 142, a rating of pump 142 (e.g., a particular pump may be rated for a maximum pump duty cycle), a duration of therapy time, an energy capacity of power source 120 (e.g., 100% charge remaining, 50% charge remaining, 50 kW-hrs remaining, etc.), a mode of operation of NPWT device 100 (e.g., standard therapy mode, seal assist mode, etc.), etc. If the pump duty cycle threshold value is determined rather than being a predetermined value, duty cycle manager 134 may be configured to determine the pump duty cycle threshold value using any of an equation, a set of equations, a lookup table, a graph, a database, a script object, a function, etc. In some embodiments, duty cycle manager 134 periodically receives/monitors pump duty cycle values of pump 142 at an end of a time step and periodically provides leak determination manager 154 with the periodic pump duty cycle values. In some embodiments, duty cycle manager 134 monitors pump duty cycle values at an end of a time step having a predetermined duration (e.g., 1 second, 5 seconds, 1 minute, etc.).

In some embodiments, duty cycle manager 134 is configured to determine a leak amount (e.g., a leak rate) based on the pump duty cycle. In some embodiment, duty cycle manager 134 uses a relationship between the pump duty cycle and leak rate to determine the leak rate. In some embodiments, the relationship is a linear relationship. In some embodiments, the relationship is a non-linear relationship. In some embodiments, the relationship can be expressed as:

$$L_{leak} = f_{leak}(PD)$$

where $L_{leak}$ is a leak rate of the NPWT, PD is a present pump duty cycle value of pump 142, and $f_{leak}$ is a relationship between the leak rate and the present pump duty cycle value. In some embodiments, $f_{leak}$ is a correlation determined based on empirical data.

In some embodiments, controller 110 is configured to receive a measured value of the leak rate from leak sensor 146. In some embodiments, leak sensor 146 is a mass air flow sensor, configured to measure a flow rate of leak at a seal. In some embodiments, leak sensor 146 is configured to provide controller 110 and leak determination manager 154 with the measured leak rate. In some embodiments, leak determination manager 154 uses one or both of the leak rate determined based on the pump duty cycle and the measured leak rate to adjust the leak alarm parameters. In some embodiments, leak sensor 146 is or includes any of a flow rate sensor and a pressure sensor. If leak sensor 146 is a pressure sensor, controller 110 can be configured to use pressure readings from the pressure sensor to determine a leak rate. If leak sensor 146 is a flow rate sensor (e.g., configured to measure flow rate of pump 142 or leakage flow rate), controller 110 can be configured to use the measurements from the flow rate sensor to determine a flow rate of leak at a seal at the wound site. In some embodiments, controller 110 is configured to operate pump 142 to achieve a target pressure at the wound site or within a negative pressure circuit that pump 142 is fluidly coupled to, and receive pressure or flow rate measurements from a pressure sensor or a flow rate sensor (e.g., leak sensor 146). In some embodiments, controller 110 is configured to compare the value of the target pressure to the monitored/measured values received from the pressure sensor or the flow rate sensor to determine a leak rate (e.g., to determine a dressing application quality).

In some embodiments, controller 110 includes GPS 316. In some embodiments, GPS 316 is configured to determine a location of NPWT device 100. In some embodiments, GPS 316 is configured to determine a location of NPWT device 100 and a direction of motion of NPWT device 100. In some embodiments, GPS 316 is configured to provide leak determination manager 154 with any of a present location of NPWT device 100, a direction of motion of NPWT device 100, a speed of motion of NPWT device 100, a proximity of NPWT device 100 to a known charging location, etc. In some embodiments, leak determination manager 154 is configured to use any of the information from GPS 316 to determine leak alarm parameter adjustments.

Referring still to FIG. 2, controller 110 is shown to include accelerometer 144, according to some embodiments. In some embodiments, accelerometer is configured to measure acceleration which indicates a motion of NPWT device 100 and therefore motion of a user of NPWT device 100. In some embodiments, accelerometer 144 is configured to provide leak determination manager 154 with an identification of whether NPWT device 100 is moving. In some embodiments, leak determination manager 154 is configured to use the detection of motion to adjust or determine adjustments for one or more leak alarm parameters.

In some embodiments, controller 110 is configured to receive information from light sensor 148. In some embodiments, light sensor 148 is configured to measure an intensity of light at or surrounding NPWT device 100. In some embodiments, light sensor 148 is configured to measure an intensity of light in direct contact with NPWT device 100. In some embodiments, light sensor 148 is a CCD light sensor. In some embodiments, light sensor 148 is an LDR light sensor. Light sensor 148 can be configured to provide leak determination manager 154 with the measured light intensity via input interface 140, according to some embodiments. In some embodiments, light sensor 148 is positioned at or on an exterior surface of housing 102 of NPWT device 100. In some embodiments, leak determination manager 154 is configured to use the measured light intensity provided by and measured by light sensor 148 to determine changes to leak alarm parameters or to update leak alarm parameters.

Referring still to FIG. 2, controller 110 is shown to include high leak mode parameters database 150 and low leak mode parameters database 152, according to some embodiments. In some embodiments, high leak mode parameters database 150 and low leak mode parameters database 152 are configured to provide leak determination manager 154 with one or more leak alarm parameters used to determine if a leak event has occurred and used to determine if a leak alarm should be provided via user interface 106. In some embodiments, the one or more leak alarm parameters include a leak threshold value. In some embodiments, the leak alarm parameters include one or more parameters for characterizing a wound application. In some embodiments, the wound application can be determined as a high leak application or a low leak application. In some embodiments, leak determination manager 154 is configured to determine if the wound application is a high leak application or a low leak application. In some embodiments, if the wound application is a high leak application, leak determination manager 154 uses leak alarm parameters from high leak mode parameters database 150. In some embodiments, if the wound application is a low leak application, leak determination manager 154 uses leak alarm parameters from low leak mode parameters database 152.

Referring still to FIG. 2, controller 110 is shown to include leak determination manager 154, according to some embodiments. In some embodiments, leak determination manager 154 is configured to receive any of power source capacity information, motion detection information, light sensor information, leakage rates, pump duty cycle, leak alarm parameters, etc., and determine if a leak alarm should be provided via user interface 106. In some embodiments, leak determination manager 154 is configured to dynamically adjust one or more leak alarm parameters while NPWT device 100 is in use. In some embodiments, leak determination manager 154 adjusts leak alarm parameters to suit individual patients, to account for situations and environmental factors, to reduce customer annoyance from excessive alarms, etc. In some embodiments, leak determination manager 154 reduces an amount of low-risk alarms, providing an overall more efficient alarm system. In some embodiments, leak determination manager 154 decreases an amount of alarms to conserve an amount of energy/charge remaining in power source 120.

In some embodiments, controller 110 is configured to receive information from one or more sensors positioned locally at a wound site. In some embodiments, a wireless sensing Magnetic Acoustic Resonance Sensor (MARS) is positioned at the wound site. In some embodiments, the wireless sensing MARS detects motion at the wound site. In some embodiments, accelerometer 144 is positioned locally at the wound site. In some embodiments, controller 110 uses a gyroscope to detect motion. In some embodiments, the gyroscope is positioned at NPWT device 100. In some embodiments, the gyroscope is positioned locally at the wound site. In some embodiments, accelerometer 144 is positioned in NPWT device 100. In some embodiments, accelerometer 144 is positioned at the wound site. Similarly, the gyroscope may be positioned in NPWT device 100 or at the wound site. The wireless sensing MARS may be positioned at the wound site or in NPWT device 100. The gyroscope and/or accelerometer 144 may be configured to wirelessly communicate measurements to controller 110.

In some embodiments, memory 116 includes a pump manager configured to adjust an operation of pump 142. In some embodiments, the pump manager is configured to use Pulse Width Modulation (PWM) to adjust a duty cycle of pump 142. In some embodiments, the pump manager is configured to adjust an operation of pump 142 in response to a determination that the application quality is a high leak rate quality. In some embodiments, the pump manager is duty cycle manager 134. In some embodiments, the pump manager decreases therapy pressure in response to the determination that the application quality is a high leak rate quality. In some embodiments, the pump manager switches to DPC or intermittent therapy in response to the determination that the application quality is a high leak rate quality to conserve energy/charge capacity of power source 120.

Leak Determination Manager

Figure 3:
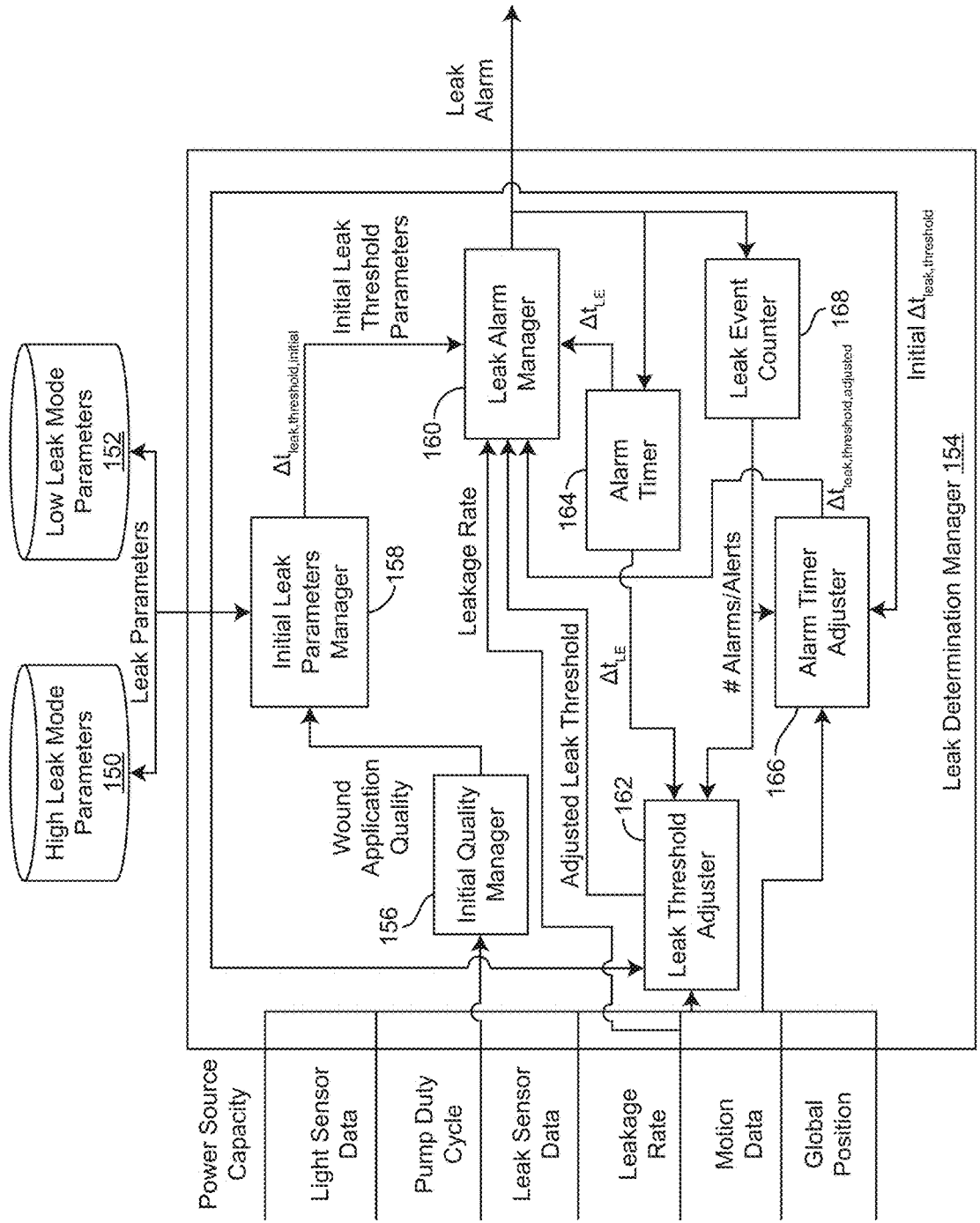
FIG. 3 is a block diagram of the leak determination manager of the controller of FIG. 1, according to some embodiments.

Referring now to FIG. 3, leak determination manager 154 is shown in greater detail, according to some embodiments. Leak determination manager 154 is configured to determine if a leak event has occurred (e.g., if a leakage rate exceeds a leak threshold value), and if a leak event has occurred, if an alert/alarm should be provided to user interface 106, according to some embodiments.

In some embodiments, leak determination manager 154 receives power source capacity information, light sensor information, leak amount information, leak sensor data/ information, global position information, motion data, pump duty cycle, etc. In some embodiments, leak determination manager 154 is configured to receive the pump duty cycle at an initial time (e.g., immediately after NPWT initiation), and characterizes the initial dressing application based on the pump duty cycle at the initial time. In some embodiments, initial quality manager 156 is configured to receive the pump duty cycle value at an initial time, and compare the initial pump duty cycle to a threshold pump duty cycle value. In some embodiments, if the initial pump duty cycle is greater than the threshold pump duty cycle value, initial quality manager 156 determines that the initial application quality is a high leak rate quality. In some embodiments, if the initial pump duty cycle is less than the threshold pump duty cycle value, initial quality manager 156 determines that the initial application quality is a low leak rate quality. As described above, the pump duty cycle is related to leak rate, according to some embodiments. Therefore, identifying a high initial pump duty cycle identifies a high initial leak rate, and identifying a low initial pump duty cycle identifies a low initial leak rate, according to some embodiments. In some embodiments, initial leak sensor data or leakage rate determined based on the initial pump duty cycle can be compared to a leak threshold value to determine the initial application quality.

In some embodiments, initial quality manager 156 is configured to characterize the initial application quality as low leak or high leak. In some embodiments, initial quality manager 156 is configured to provide initial leak parameters manager 158 with the characterized initial application quality. In some embodiments, initial leak parameters manager 158 is configured to receive one or more leak parameters from high leak mode parameters database 150 and low leak mode parameters database 152 and select either high leak mode parameters or low leak mode parameters based on the initial application quality. In some embodiments, if the initial application quality as determined by initial quality manager 156 is a high initial leak quality, initial leak parameters manager 158 selects leak parameters from high leak mode parameters database 150. Likewise, if the initial application quality as determined by initial quality manager 156 is a low initial leak quality, initial leak parameters manager 158 selects leak parameters from low leak mode parameters database 152, according to some embodiments.

In some embodiments, the leak parameters from either high leak mode parameters database 150 or low leak mode parameters database 152 include a leak threshold value $L_{threshold}$. In some embodiments, the leak threshold value is used to determine if a leak (e.g., a leakage rate) exceeds the leak threshold value. In some embodiments, if the leak exceeds the leak threshold value, a leak event has occurred. In some embodiments, the leak threshold value from high leak mode parameters database 150 is referred to as $L_{high,threshold}$ and the leak threshold value from low leak mode parameters database 152 is referred to as $L_{low,threshold}$. In some embodiments, $L_{high,threshold}$ is 2000 cc/min. In some embodiments, $L_{low,threshold}$ is 200 cc/min. In some embodiments, initial leak parameters manager 158 receives an alarm timer threshold value $\Delta t_{leak,threshold}$ from high leak mode parameters database 150 and/or low leak mode parameters database 152. In some embodiments, the alarm timer threshold value from high leak mode parameters database 150 is referred to as $\Delta t_{leak,threshold,high}$ and the alarm timer threshold value from low leak mode parameters database 152 is referred to as $\Delta t_{leak,threshold,low}$. In some embodiments, $\Delta t_{leak,threshold,high}$ is 60 minutes. In some embodiments, $\Delta t_{leak,threshold,low}$ is 5 minutes. In some embodiments, the alarm timer threshold values are used to determine if the leak threshold parameters should be changed (e.g., increased or decreased). In some embodiments, the alarm timer threshold value is compared to a time between subsequently occurring leak alarms. In some embodiments, if the subsequently occurring leak alarms are spaced apart in time less than $\Delta t_{leak,threshold}$, the leak threshold value is increased. In some embodiments, if the subsequently occurring leak alarm are spaced apart in time greater than $\Delta t_{leak,threshold}$, the leak threshold value is either decreased or remains the same. In some embodiments, initial leak parameters manager 158 receives a predetermined cumulative threshold value $LA_{total,threshold}$ which indicates a maximum amount of alarms which may be provided over a time period (e.g., 5 alarms per hour).

Referring still to FIG. 3, leak determination manager 154 is shown to include leak alarm manager 160, according to some embodiments. In some embodiments, leak alarm manager 160 is configured to receive a present leakage rate (e.g., leakage rate as determined from pump duty cycle, or as measured by leak sensor 146), $L_{present}$ or simply L, and compare the present leakage rate to the leak threshold value. In some embodiments, if the present leakage rate $L_{present}$ exceeds the leak threshold value $L_{threshold}$, leak alarm manager 160 determines that a leak event has occurred. In some embodiments, if the present leakage rate is less than the leak threshold value, leak alarm manager 160 determines that a leak event has not occurred. In some embodiments, if present leakage rate exceeds the leak threshold value, leak alarm manager 160 outputs a leak alarm to user interface manager 107. In some embodiments, if present leakage rate exceeds the leak threshold value, but one or more conditions have not been satisfied (e.g., a total number of leak events over a previous time period is not greater than a leak event threshold value), leak alarm manager 160 determines that a leak event has occurred but does not output a leak alarm to user interface manager 107. In some embodiments, leak alarm manager 160 outputs the leak event to leak event counter 168 without outputting a leak alarm to user interface manager 107. In some embodiments, leak alarm manager 160 outputs the leak event to leak event counter 168 and also outputs the leak alarm to user interface manager 107. In some embodiments, the leak event indicates whether the present leakage rate exceeds the leak threshold value, however, the occurrence of a leak event does not necessarily indicate a leak alarm.

In some embodiments, leak alarm manager 160 outputs a leak alarm to user interface manager 107 if a time interval between subsequently occurring leak alarms and/or leak events is less than a predetermined time interval threshold value, $\Delta t_{leak,threshold}$. In some embodiments, the time interval between subsequently occurring leak alarms and/or leak events indicates a frequency of alarms provided to user interface manager 107 which are provided to user interface 106. In some embodiments, in order to decrease an amount of alarms provided to a user, leak alarm manager 160 compares the time interval between subsequently occurring leak alarms and/or leak events to the predetermined time interval threshold value to determine if a leak alarm should be provided to user interface manager 107. In this way, if alarms/alerts are occurring frequently, leak alarm manager 160 may only provide leak alarms to user interface manager 107 if a predetermined amount of time has passed since the previous leak alarm provided to user interface manager 107 (e.g., 5 minutes, 60 minutes, etc.). In some embodiments, an initial time interval threshold value $\Delta t_{leak,threshold,initial}$ is provided to leak alarm manager 160 by initial leak parameters manager 158. In some embodiments, $\Delta t_{leak,threshold,initial}$ is 5 minutes if initial quality manager 156 determines a low leak rate quality. In some embodiments, $\Delta t_{leak,threshold,initial}$ is 60 minutes if initial quality manager 156 determines a high leak rate quality. In this way, if initial quality manager 156 determines that a large amount of leakage is present (i.e., high leak rate quality) initially, leak alarm manager 160 can reduce an amount of alarms by constraining the leak alarms provided to user interface manager 107 to every $\Delta t_{leak,threshold,initial}$ (every 60 minutes, every 5 minutes, etc.), according to some embodiments.

Referring still to FIG. 3, leak determination manager 154 is shown to include leak event counter 168, according to some embodiments. In some embodiments, leak event counter 168 is configured to count a number of leak events output by leak alarm manager 160 or a number of leak alarms output by leak alarm manager 160 to user interface manager 107. In some embodiments, leak event counter 168 counts a total number of leak events and/or leak alarms since NPWT has been initiated. In some embodiments, leak event counter 168 counts a number of leak events and/or leak alarms over a previous time period. In some embodiments, leak event counter 168 is a rolling counter for a predetermined time period. For example, leak event counter 168 may count a number of leak events and/or leak alarms over the previous hour, the previous half hour, the previous two hours, etc., according to some embodiments. In some embodiments, leak event counter 168 counts a number of leak events and/or leak alarms over a previous time period $t_{count}$. In some embodiments, at an end of a time increment, leak event counter 168 checks if it has received a leak event and/or leak alarm indication from leak alarm manager 160. In some embodiments, the time increment is $\Delta t$. In some embodiments, the time increment $\Delta t$ is 1 minute, 10 seconds, 30 seconds, etc. For example, if the time increment $\Delta t$ is 1 minute and leak alarm manager 160 keeps a count of a number of alarms/events over the past hour, leak event counter 168 may store a number leak events and/or leak alarms from $t=0$ to $t=-60\Delta t$. In some embodiments, leak alarm manager 160 determines a cumulative amount of leak alarms and/or leak events over the previous time period using at least one of the equations:

$$LE_{total} = \sum_{i=0}^{i=\frac{\Delta t_{total}}{\Delta t}} LE(t = -i\Delta t)$$

$$LA_{total} = \sum_{i=0}^{i=\frac{\Delta t_{total}}{\Delta t}} LA(t = -i\Delta t)$$

where $LE_{total}$ and $LA_{total}$ are a total number of leak events and leak alarms, respectively, over time period $\Delta t_{total}$ (e.g., 1 hour), $LE(t=-i\Delta t)$ and $LA(t=-i\Delta t)$ are leak event and leak alarm at time $-i\Delta t$ (e.g., when $i=0$, $t=0$), and $\Delta t$ is a time increment (e.g., 1 minute).

In some embodiments, leak determination manager 154 includes alarm timer 164, according to some embodiments. In some embodiments, alarm timer 164 is configured to determine an amount of time between subsequently occurring leak alarms and/or leak events. In some embodiments, alarm timer 164 receives the determined leak alarm and/or leak event from leak alarm manager 160 and records a time at which the determined leak alarm and/or leak event occurred. In some embodiments, alarm timer 164 receives a next leak alarm and/or leak event and records a time at which the next leak alarm and/or leak event occurred. In some embodiments alarm timer 164 determines a time interval between the subsequently occurring leak alarms and/or leak events, $\Delta t_{LE}$ and/or $\Delta t_{LE}$. In some embodiments, alarm timer 164 determines an average time interval between subsequently occurring leak alarms and/or leak events, $\overline{\Delta t_{LE}}$ and/or $\overline{\Delta t_{LE}}$ over a previous time period. In some embodiments, the previous time period is the same time period as the cumulative/total amount of leak alarms and/or leak events as counted by leak event counter 168 (e.g., 1 hour, 30 minutes, etc.).

In some embodiments, leak event counter 168 provides the cumulative number of leak events and/or leak alarms over the previous time period to leak threshold adjuster 162 and alarm timer adjuster 166. In some embodiments, leak threshold adjuster 162 and alarm timer adjuster 166 use the cumulative number of leak events and/or leak alarms over the previous time period to adjust the leak threshold value and/or the alarm timer threshold value. In some embodiments, if the cumulative number of leak events and/or leak alarms over the previous time period exceed a predetermined counter threshold value, leak threshold adjuster 162 increases the leak threshold value to decrease an amount of leak alarms and/or leak events. In this way, leak threshold adjuster 162 adjusts the leak threshold value based on the cumulative number of leak events and/or leak alarms to decrease an overall sensitivity of leak alarm manager 160, producing less leak alarms and/or less leak events.

In some embodiments, alarm timer 164 provides leak threshold adjuster 162 with the time interval between subsequently occurring leak alarms and/or leak events, and/or the average time interval between subsequently occurring leak alarms and/or leak events. In some embodiments, leak threshold adjuster 162 uses either the time interval and/or the average time interval between subsequently occurring leak alarms and/or leak events over the previous time period to determine an adjustment for the leak threshold value.

In some embodiments, leak threshold adjuster 162 receives leak threshold parameters from high leak mode parameters database 150 and/or low leak mode parameters database 152. In some embodiments, leak threshold adjuster 162 adjusts $\Delta t_{leak,threshold}$ and $L_{threshold}$ of leak alarm manager 160 based on at least one of a number of alarms/alerts over a previous time period received from leak event counter 168, and a time interval between a previous leak alarm and a present time received from alarm timer 164. In some embodiments, if the amount of time since the previous leak alarm is equal to or exceeds $\Delta t_{leak,threshold}$ and the total number of leak alarms and/or leak events over the previous time period (e.g., $LA_{total}$) exceeds a counter threshold value, leak threshold adjuster 162 increases $L_{threshold}$ and/or $\Delta t_{leak,threshold}$. In some embodiments, leak threshold adjuster 162 increases $L_{threshold}$ from $L_{low,threshold}$ to $L_{high,threshold}$, if leak alarm manager 160 is currently set at $L_{low,threshold}$. In some embodiments, leak threshold adjuster 162 increases $L_{threshold}$ of leak alarm manager 160 from $L_{low,threshold}$ to $L_{high,threshold}$ in response to a total/cumulative number of alarms/alerts exceeding a predetermined cumulative threshold value $LA_{total,threshold}$ (e.g., 5 alarms per hour).

The function of leak event counter 168 and/or alarm timer 164 can be understood with reference to FIGS. 5-8, according to some embodiments. FIG. 5 shows leak alarms 502*a-g* output by leak alarm manager 160 over a time period, according to some embodiments. In some embodiments, the Y-axis of graph 500 indicates whether leak alarm manager 160 output a leak alarm at that particular point in time. In some embodiments, the X-axis of graph 500 indicates time, with t(k) representing a present point in time. In some embodiments, leak event counter 168 counts a total number of alarms output by leak alarm manager 160 over time period 508. In some embodiments, time period 508 has a time duration 506. In some embodiments, time period 508 ranges from t(k) to t(k−15), where t(k−15) is 15 time increments before t(k). As shown in FIG. 5, leak event counter 168 would count a total of 3 alarms before t(k), according to some embodiments. In some embodiments, if the total number of alarms over time period 508 exceeds a counter threshold value (e.g., 5 alarms), leak threshold adjuster 162 increases the leak threshold value to decrease a number of alarms. For example, as shown in FIG. 6, time period 508 includes 6 alarms, according to some embodiments. In some embodiments, if the counter threshold value is 5 alarms per time duration 506, leak threshold adjuster 162 would increase the leak threshold parameters for the example shown in FIG. 6. In some embodiments, for the example shown in FIG. 6, if the counter threshold value is 5 alarms per time duration 506, leak threshold adjuster 162 would increase $L_{threshold}$ of leak alarm manager 160 from $L_{low,threshold}$ to $L_{high,threshold}$, or vice versa, to decrease an amount of alarms for future operation.

Referring still to FIG. 5, graph 500 is shown to include leak alarm 502*h* at the present moment t(k), according to some embodiments. In some embodiments, before leak alarm 502*h* is provided to user interface manager 107, a time duration 510 between time t(k) (the present moment) and the previous leak alarm 502*g* is determined. In some embodiments, if time duration 510 is not equal to or greater than $\Delta t_{leak,threshold}$ (e.g., 5 minutes for low leak quality, 60 minutes for high leak quality), leak alarm 502*h* is not provided to user interface manager 107. In some embodiments, if time duration 510 is greater than or equal to $\Delta t_{leak,threshold}$, leak alarm 502*h* is output to user interface manager 107. In some embodiments, $\Delta t_{leak,threshold}$ is increased or decreased in response to the number of alarms within time period 508. For example, if the number of alarms within time period 508 exceeds a predetermined threshold value, $\Delta t_{leak,threshold}$ may be increased so that leak alarms 502 are provided to user interface manager 107 and therefore display to a user/patient less frequently.

Referring now to FIG. 7, in some embodiments, time period 508 has time duration 506, shown as less than time duration 506 in FIGS. 5-6. In some embodiments, time duration 506 may be increased or decreased so that time period 508 covers a greater or less amount of time over which leak alarms 502 are counted. In some embodiments, time duration 506 may be increased or decreased in response to the number of leak alarms 502 within time period 508 exceeding a predetermined threshold value. In this way, time duration 506 may be adjusted instead of adjusting $LA_{total,threshold}$.

Referring now to FIGS. 8-9, graphs 500D and 500E show leak alarms 502 provided to user interface manager 107 before and after $\Delta t_{leak,threshold}$ has been adjusted, according to some embodiments. In some embodiments, as shown in FIG. 8, leak alarms 502 occur every time interval/duration 504. In some embodiments, graph 500D represents leak events (e.g., leakage rate exceeding $L_{threshold}$) occurring at every time step, but only provided as leak alarms after an amount of time equal to time duration 504 has passed between subsequent leak events. In some embodiments, graph 500D represents $\Delta t_{leak,threshold}$ equal to time duration 504. In some embodiments, graph 500E of FIG. 9 represents after $\Delta t_{leak,threshold}$ has been increased. In this way, leak events may occur at every time step of graph 500E, but leak alarms 502 are only provided to user interface manager 107 and/or user interface 106 after time duration 505 has passed, according to some embodiments. In some embodiments, increasing $\Delta t_{leak,threshold}$ decreases an amount of leak alarms 502 provided to user interface manager 107 and/or user interface 106 over a time period (e.g., time period 508). For example, as shown in FIG. 8, seven leak alarms 502 are output over time period 508, while in FIG. 9 after $\Delta t_{leak,threshold}$ has been increased, only four leak alarms 502 are output over time period 508.

Referring again to FIG. 3, leak threshold adjuster 162 and alarm time adjuster 166 are shown receiving any of power source capacity, light sensor data, leak sensor data, leakage rate, motion data, and global position, according to some embodiments. In some embodiments, either of leak threshold adjuster 162 or alarm time adjuster 166 use the received information to determine leak threshold adjustments (e.g., an increase or decrease of $L_{threshold}$) and/or $\Delta t_{leak,threshold}$ adjustments. In some embodiments, leak threshold adjuster 162 increases $L_{threshold}$ to decrease a number of leak alarms in response to power source capacity decreasing or in response to power source capacity falling below a threshold value. For example, if power source capacity is less than 20%, leak threshold adjuster 162 may increase $L_{threshold}$ so that only leak events which indicate a very high amount of leakage (e.g., 2000 cc/min) produce a leak alarm. In some embodiments, leak threshold adjuster 162 increases $L_{threshold}$ relative to an initial $L_{threshold}$ value. For example, if $L_{threshold}$ was initially set to $L_{low,threshold}$, leak threshold adjuster 162 may increase $L_{threshold}$ from $L_{low,threshold}$ to $L_{high,threshold}$ in response to the power source capacity falling below a predetermined threshold value. In this way, a number of leak alarms per time period may be decreased. Additionally, increasing $L_{threshold}$ may conserve power source capacity by only outputting leak alarms if the leakage rate is excessively or unusually high, according to some embodiments.

In some embodiments, alarm time adjuster 166 adjusts (e.g., increases or decreases) $\Delta t_{leak,threshold}$ based on the power source capacity. In some embodiments, alarm time adjuster 166 increases $\Delta t_{leak,threshold}$ in response to the power source capacity decreasing or in response to the power source capacity falling below a threshold value. For example, in some embodiments, alarm timer adjuster 166 increases $\Delta t_{leak,threshold}$ so that leak alarms are output less frequently in response to the power source capacity falling below a threshold value (e.g., 20%, 30%, 50%, etc.). In some embodiments, alarm time adjuster 166 adjusts $\Delta t_{leak,threshold}$ from a first predefined value to a second predefined value (e.g., from a low leak mode $\Delta t_{leak,threshold}$ to a high leak mode $\Delta t_{leak,threshold}$). For example, alarm timer adjuster 166 may adjust $\Delta t_{leak,threshold}$ from 5 minutes to 60 minutes in response to the power source capacity falling below a threshold value (e.g., 20%) or in response to a number of leak alarms over a previous time period exceeding a threshold value (e.g., $LA_{total}$ exceeding $LA_{total,threshold}$), or in response to both the power source capacity falling below the threshold value and the number of leak alarms over the previous time period exceeding the threshold value. Advantageously, increasing $\Delta t_{leak,threshold}$ based on power source capacity may conserve power source, according to some embodiments.

In some embodiments, leak threshold adjuster 162 and alarm time adjuster 166 increase $L_{threshold}$ and/or $\Delta t_{leak,threshold}$, respectively, based on the global position of NPWT device 100. In some embodiments, leak threshold adjuster 162 and/or alarm time adjuster 166 increase $L_{threshold}$ and/or $\Delta t_{leak,threshold}$ in response to information from GPS 316 and/or a user device which indicates that the user and NPWT device 100 are moving towards a known charging location. For example, if a user/patient is travelling towards home where NPWT device 100 can be charged, leak threshold adjuster 162 and alarm time adjuster 166 may adjust $L_{threshold}$ and/or $\Delta t_{leak,threshold}$, according to some embodiments. In some embodiments, leak threshold adjuster 162 and alarm time adjuster 166 increase $L_{threshold}$ and/or $\Delta t_{leak,threshold}$ in response to the user travelling towards a known charging location. In some embodiments, $L_{threshold}$ and/or $\Delta t_{leak,threshold}$ are increased until the user is near the known charging location. In some embodiments, after the user is near the known charging location, $\Delta t_{leak,threshold}$ and/or $L_{threshold}$ may be decreased. Likewise, if the user is travelling away from the known charging location (e.g., travelling away from home), and the leakage rate or leak sensor data increases (i.e., dressing leak worsens), $L_{threshold}$ and/or $\Delta t_{leak,threshold}$ may decrease to provide the user with more frequent leak alarms so that the user fixes the leak, or to notify the user to be mindful of power source capacity (e.g., battery levels), according to some embodiments. In some embodiments, user interface manager 107 may cause user interface 106 to display a message indicating if there is a sufficient power source capacity given estimated travel time to the known charging location. In some embodiments, this facilitates notifying the user if the current travel time/distance is such that NPWT device 100 is at risk of running out of power source capacity. Advantageously, increasing $L_{threshold}$ and/or $\Delta t_{leak,threshold}$ as the user is travelling towards a known charging location reduces a number of alarms which may likely be disregarded by the user.

In some embodiments, leak threshold adjuster 162 and alarm time adjuster 166 adjust $L_{threshold}$ and/or $\Delta t_{leak,threshold}$ respectively based on motion data and/or light sensor data. In some embodiments, the motion data and/or the light sensor data indicate an environment of NPWT device 100. For example, low light intensity may indicate that the user of NPWT device 100 is sleeping, at a cinema, or in another situation/environment which should not be disturbed, according to some embodiments. In some embodiments, $L_{threshold}$ and/or $\Delta t_{leak,threshold}$ are adjusted based on the motion data and/or the light sensor data. In some embodiments, $L_{threshold}$ and/or $\Delta t_{leak,threshold}$ are increased or decreased based on the light sensor data and/or the motion data. In some embodiments, if controller 110 detects motion (e.g., from accelerometer 144), $L_{threshold}$ and/or $\Delta t_{leak,threshold}$ are increased to reduce an amount of alarms.

Advantageously, using the various sensory inputs to adjust $L_{threshold}$ and/or $\Delta t_{leak,threshold}$ provides an alarm system which dynamically adjusts alarm parameters based on initial wound application quality, environment/situation, power source capacity, etc. This reduces a number of alarms which the user would likely disregard, increases user compliance, and facilitates tailoring leak alarm parameters/triggers to specific situations, according to some embodiments.

In some embodiments, leak determination manager 154 includes a clock to track a time of day. In some embodiments, $L_{threshold}$ and/or $\Delta t_{leak,threshold}$ are adjusted based on the time of day. For example, $L_{threshold}$ and/or $\Delta t_{leak,threshold}$ may be increased during night-time to prevent alarms from disrupting the user.

Control Algorithm Method

Figure 10A:
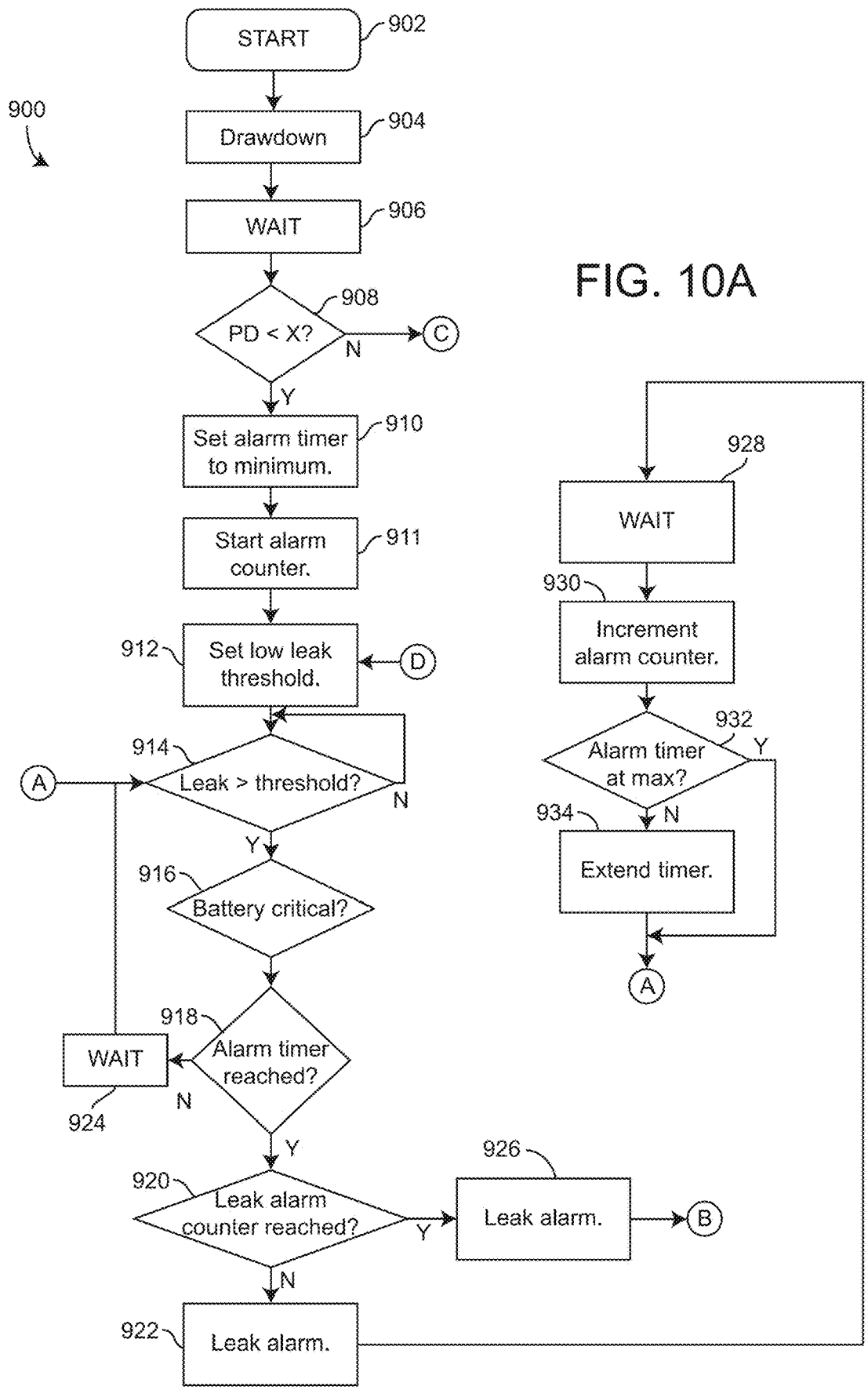
FIGS. 10A and 10B are a flow diagram illustrating a method for adjusting one or more leak alarm parameters of a NPWT device, according to some embodiments.
Figure 10B:
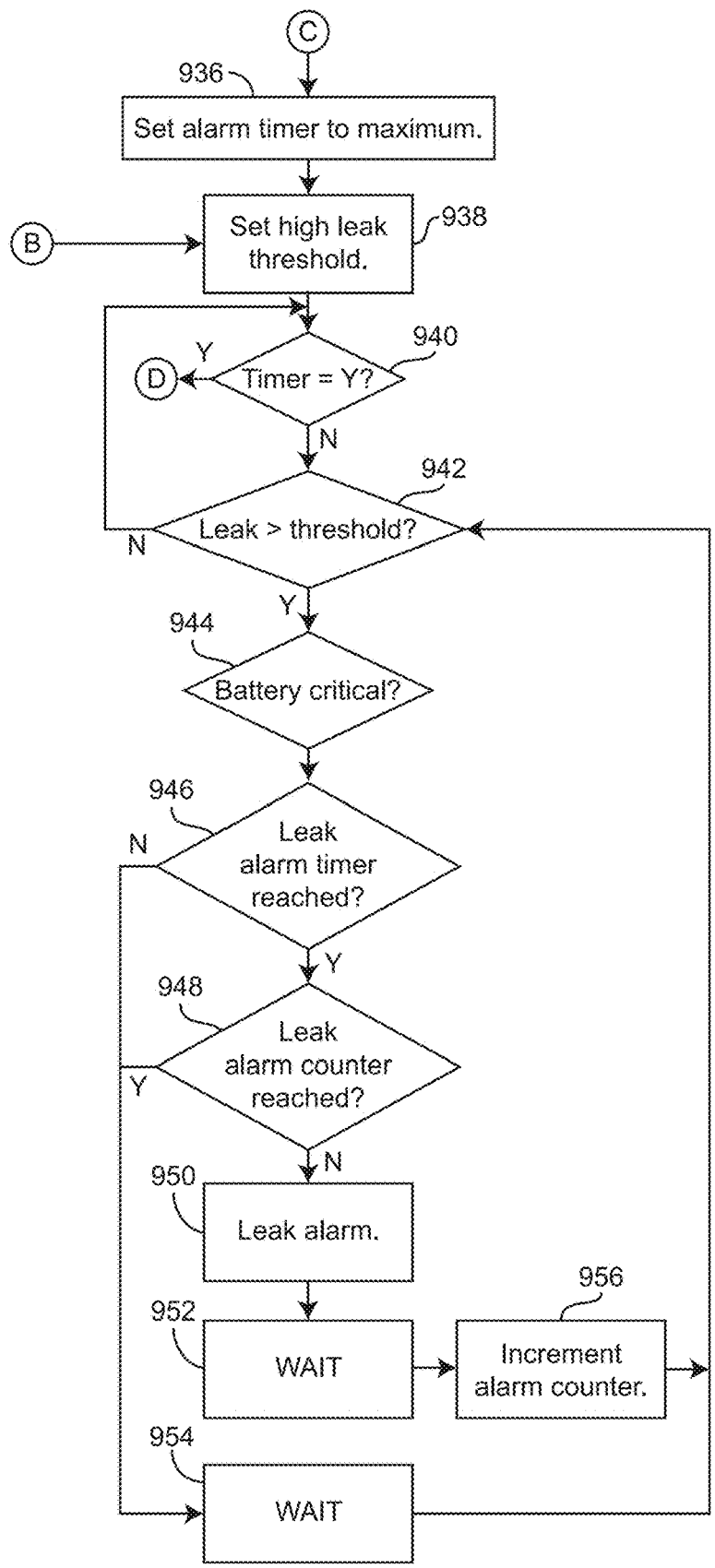

Referring now to FIGS. 10A-10B, method 900 for adjusting leak parameters is shown, according to some embodiments. In some embodiments, method 900 includes steps 902-956. In some embodiments, method 900 is performed by controller 110. In some embodiments, method 900 is performed by leak determination manager 154.

Method 900 includes starting (step 902) and drawing down (step 904) NPWT device 100, according to some embodiments. In some embodiments, NPWT device 100 is started and drawn down by controller 110. In some embodiments, drawing down NPWT device 100 includes adjusting an operation of pump 142 to increase therapy pressure over a time period to produce a seal between wound dressings and a wound. In some embodiments, pump 142 holds the increased pressure for a predetermine amount of time. In some embodiments, pump 142 decreases the therapy pressure in response to holding the pressure for the predetermined amount of time. Method 900 includes waiting a predetermined amount of time (step 906), according to some embodiments. In some embodiments, step 906 is performed to ensure that the pressure can be held.

Method 900 includes determining if pump duty value (PD) is less than a threshold value X (step 908), according to some embodiments. In some embodiments, step 908 is performed by initial quality manager 156. If the pump duty value is less than the threshold value, method 900 proceeds to step 910, according to some embodiments. If the pump duty value is greater than the threshold value, method 900 proceeds to step 936, according to some embodiments. In some embodiments, if the pump duty value is greater than the threshold value, the wound dressing application is a high leak quality application. In some embodiments, if the pump duty value is less than or equal to the threshold value, the wound dressing application is a low leak quality application.

Method 900 includes setting an alarm timer to a minimum value (step 910), according to some embodiments. In some embodiments, step 910 includes setting $\Delta t_{leak,threshold}$ equal to $\Delta t_{leak,threshold}$. In this way, alarms are only output if the previous alarm was output at a time $\Delta t_{leak,threshold}$ before a current point in time, or if the previous alarm was output at a time more than $\Delta t_{leak,threshold}$ before the present point in time. In some embodiments, step 910 is performed by initial leak parameters manager 158 and leak alarm manager 160.

Method 900 includes starting an alarm counter (step 911), according to some embodiments. In some embodiments, the alarm counter is started at an initial value of zero. In some embodiments, the alarm counter is a rolling counter, which sums a total number of alarms over a previous time period (e.g., 10 minutes, 1 hour, 2 hours, etc.). In some embodiments, the alarm counter is a combination of one or more rolling counters configured to count a total number of alarms over different time periods (e.g., a first counter counts the number of alarms over the previous 10 minutes, a second counter counts the number of alarms over the previous 1 hour, a third counter counts the number of alarms over the previous 2 hours, etc.).

Method 900 includes setting a low leak threshold (step 912), according to some embodiments. In some embodiments, step 912 includes setting $L_{threshold}$ equal to $L_{low,threshold}$ (e.g., 200 cc/min). In some embodiments, step 912 is performed by initial leak parameters manager 158 and leak alarm manager 160. In some embodiments, $L_{threshold}$ is used to determine if a current leak value exceeds $L_{threshold}$ and if a leak alarm should be output.

Method 900 includes step 914 of checking if a current leak value (e.g., L) is greater than the leak threshold value (i.e., $L_{threshold}$ as set in step 912), according to some embodiments. In some embodiments, step 914 includes comparing any of a leak value determined based on pump duty or a measured leak value to the leak threshold value $L_{threshold}$. In some embodiments, step 914 is performed by leak alarm manager 160. If the current leak value is not greater than the leak threshold value, NPWT continues, and step 914 is repeated until it is determined that the current leak value exceeds the leak threshold value $L_{threshold}$. If the current leak value exceeds the leak threshold value, method 900 proceeds to step 916.

Method 900 includes checking if a battery (e.g., power source 120) of NPWT device 100 is at a critical level (step 916), according to some embodiments. In some embodiments, the critical level is a remaining amount of energy or a remaining amount of charge in the battery (e.g., 20%, 30%, etc.). In some embodiments, the battery level (e.g., power source capacity) can be used to determine adjustments to $L_{threshold}$ and/or $\Delta t_{leak,threshold}$. In some embodiments, step 916 is performed by power source capacity manager 130.

Method 900 includes checking if $\Delta t_{leak,threshold}$ has been reached (step 918), according to some embodiments. In some embodiments, step 918 includes monitoring an amount of time which has passed since a previous leak alarm (or since step 910). In some embodiments, if the amount of time which has passed since the previous leak alarm is less than $\Delta t_{leak,threshold}$, method 900 proceeds to step 924 (step 924 includes waiting some amount of time), and then to step 914. In some embodiments, if the amount of time which has passed since the previous leak alarm (or since step 910 for a first time performing step 918) is equal to or greater than $\Delta t_{leak,threshold}$, method 900 proceeds to step 920. In some embodiments, step 918 is performed by any of alarm timer 164 and leak alarm manager 160 or a combination of leak alarm manager 160 and alarm timer 164.

Method 900 includes determining if a leak alarm counter has reached a threshold value (step 920), according to some embodiments. In some embodiments, step 920 includes comparing a total number of leak alarms over a previous time period (e.g., $LA_{total}$) and comparing the total number of leak alarms over the previous time period to a threshold value (e.g., $LA_{total,threshold}$). In some embodiments, if the total number of leak alarms over the previous time period exceeds or is equal to the threshold value, method 900 proceeds to step 926. In some embodiments, if the total number of leak alarms over the previous time period is less than the threshold value, method 900 proceeds to step 922. In some embodiments, the total number of leak alarms is a rolling count of leak alarms over the previous time period with respect to a present point in time.

Method 900 includes providing a leak alarm (steps 926 and step 922), according to some embodiments. In some embodiments, step 926 and step 922 are performed by user interface 106 and facilitated by user interface manager 107. In some embodiments, the leak alarm includes an indication of a cause of the leak alarm. For example, the leak alarm may include a message, notification, or text which indicates that the leak alarm is due to the current leak rate exceeding the leak threshold value as well as the total number of leak alarms over the previous time period (e.g., $LA_{total}$) exceeding the threshold value (e.g., $LA_{total,threshold}$) (step 926), according to some embodiments.

In some embodiments, if the total number of leak alarms over the previous time period does not exceed the threshold value (step 920), method 900 proceeds to step 922 and then step 928. In some embodiments, step 928 includes waiting for a period of time. In some embodiments, after completing step 928, method 900 proceeds to step 930. Step 930 includes incrementing an alarm counter in response to the leak alarm (step 922), according to some embodiments. In some embodiments, step 930 includes incrementing a rolling alarm counter over the previous time period (e.g., incrementing $LA_{total}$) In some embodiments, step 930 is performed by leak event counter 168. In some embodiments, method 900 proceeds to step 914 after completing step 930. In some embodiments, method 900 proceeds to step 932 in response to performing step 930.

Method 900 includes determining if the leak alarm timer (e.g., $\Delta t_{leak,threshold}$) is at a maximum value (step 932), according to some embodiments. In some embodiments, if the leak alarm timer is not at the maximum value, method 900 proceeds to step 934 where the leak alarm timer (e.g., $\Delta t_{leak,threshold}$) is extended. In some embodiments, if the leak alarm timer is at the maximum value, method 900 proceeds to step 914. In some embodiments, the leak alarm timer is extended (step 934) to conserve capacity of power source 120. For example, if power source 120 is a portable power source (e.g., a battery), the leak alarm timer may be increased so that the battery does not quickly become drained due to an excessive and unnecessary amount of alarms, according to some embodiments. In some embodiments, the leak alarm timer is increased based on a type of power source 120 connected (e.g., MAINS power, battery power, etc.) and an amount of power remaining in power source 120 (e.g., 50% charge/power remaining, 20% charge/power remaining, etc.). For example, since a leak alarm has already been provided to the user at step 922, any additional alarms may be unnecessary, since the alarm has already been provided to the user. Advantageously, step 934 facilitates a reduction of alarms which the user may consider annoying. In some embodiments, step 934 includes decreasing the alarm timer if the current leak has increased above a predetermined threshold value.

If the pump duty value (step 908) is not less than the threshold pump duty value (e.g., X), method 900 proceeds to step 936, according to some embodiments. In some embodiments, step 936 includes setting the alarm timer (e.g., $\Delta t_{leak,threshold}$) equal to a maximum alarm timer value (e.g., 60 minutes). In some embodiments, step 936 is performed by alarm timer adjuster 166.

Method 900 includes setting a high leak threshold value (step 938), according to some embodiments. In some embodiments, step 938 includes setting $L_{threshold}$ equal to $L_{high,threshold}$ (e.g., 2000 cc/min). In some embodiments, step 938 includes increasing $L_{threshold}$ by some amount. In some embodiments, step 938 is performed by leak threshold adjuster 162. In some embodiments, method 900 proceeds to step 940 in response to completing step 938.

Method 900 includes determining if a timer is equal to a threshold value Y (step 940), according to some embodiments. In some embodiments, the timer is an amount of time which method 900 has been performing steps 940-942 without the leak rate L exceeding $L_{threshold}$. In some embodiments, step 940 is performed by any of leak threshold adjuster 162, alarm timer 164, or another timer (e.g., a clock). In some embodiments, the timer is initiated at step 938. In some embodiments, the timer is reset if the conditions described with reference to step 942 are met.

Method 900 includes checking if a current leak value (e.g., L) is greater than the leak threshold value as set in step 938 (step 942), according to some embodiments. In some embodiments, if the current leak value does not exceed/is not greater than the leak threshold value as set in step 938, method 900 returns to step 940. In some embodiments, if the current leak value is greater than the threshold value as set in step 938, method 900 proceeds to step 944. In some embodiments, step 942 is performed by leak alarm manager 160. In some embodiments, step 942 includes determining if a number of leak alarms over a previous time period is less than a threshold value. In some embodiments, if the number of leak alarms over the previous time period is less than the threshold value, method 900 returns to step 940.

Steps 940-942 of method 900 provide a loop which continually checks at least one of a current leak value and a number of alarms for time Y, according to some embodiments. If the current leak value and the number of alarms for time Y do not exceed a threshold value (e.g., a threshold leak value and/or a threshold number of alarms value), method 900 returns to step 912, according to some embodiments. In some embodiments, if the current leak value and the number of alarms for time Y do not exceed the threshold value(s), it is determined that the dressing seal has improved (e.g., a lower leak rate), and that the leak threshold $L_{threshold}$ can be reset to a low leak threshold value.

Method 900 includes checking if a battery (e.g., power source 120) of NPWT device 100 is at a critical level (step 944), according to some embodiments. In some embodiments, the critical level is a remaining amount of energy or a remaining amount of charge in the battery (e.g., 20%, 30%, etc.). In some embodiments, the battery level (e.g., power source capacity) can be used to determine adjustments to $L_{threshold}$ and/or $\Delta t_{leak,threshold}$. In some embodiments, step 944 is performed by power source capacity manager 130.

Method 900 includes checking if $\Delta t_{leak,threshold}$ has been reached (step 946), according to some embodiments. In some embodiments, step 946 includes monitoring an amount of time which has passed since a previous leak alarm. In some embodiments, if the amount of time which has passed since the previous leak alarm is less than $\Delta t_{leak,threshold}$, method 900 proceeds to step 954 (step 954 includes waiting some amount of time), and then back to step 942. In some embodiments, if the amount of time which has passed since the previous leak alarm is equal to or greater than $\Delta t_{leak,threshold}$, method 900 proceeds to step 948. In some embodiments, step 946 is performed by any of alarm timer 164 and leak alarm manager 160 or a combination of leak alarm manager 160 and alarm timer 164.

Method 900 includes determining if a leak alarm counter has reached a threshold value (step 948), according to some embodiments. In some embodiments, step 948 includes comparing a total number of leak alarms over a previous time period (e.g., $LA_{total}$) and comparing the total number of leak alarms over the previous time period to a threshold value (e.g., $LA_{total,threshold}$) In some embodiments, if the total number of leak alarms over the previous time period exceeds or is equal to the threshold value, method 900 proceeds to step 954. In some embodiments, if the total number of leak alarms over the previous time period is less than the threshold value, method 900 proceeds to step 950. In some embodiments, the total number of leak alarms is a rolling count of leak alarms over the previous time period with respect to a present point in time.

Method 900 includes providing a leak alarm (steps 950), according to some embodiments. In some embodiments, step 950 are performed by user interface 106 and facilitated by user interface manager 107. In some embodiments, the leak alarm includes an indication of a cause of the leak alarm. For example, the leak alarm may include a message, notification, or text which indicates that the leak alarm is due to the current leak rate exceeding the leak threshold value as well as the total number of leak alarms over the previous time period (e.g., $LA_{total}$) exceeding the threshold value (e.g., $LA_{total,threshold}$) (step 948), according to some embodiments.

Method 900 includes waiting an amount of time (step 952) in response to completing step 950, according to some embodiments. In some embodiments, method 900 proceeds to step 956 in response to waiting the amount of time. Step 930 includes incrementing an alarm counter in response to the leak alarm (step 950), according to some embodiments. In some embodiments, step 956 includes incrementing a rolling alarm counter over the previous time period (e.g., incrementing $LA_{total}$) In some embodiments, step 956 is performed by leak event counter 168. In some embodiments, method 900 returns to step 942 after completing step 956.

Method 900 can be used to dynamically adjust one or more alarm parameters (e.g., $LA_{total,threshold}$, $\Delta t_{leak,threshold}$, $L_{threshold}$), according to some embodiments. In some embodiments, dynamically adjusting the one or more alarm parameters reduces a number of alarms and tailors alarms to the specific implementation/application of NPWT device 100.

Pulse Width Modulation and Duty Cycle Examples

Figure 11:
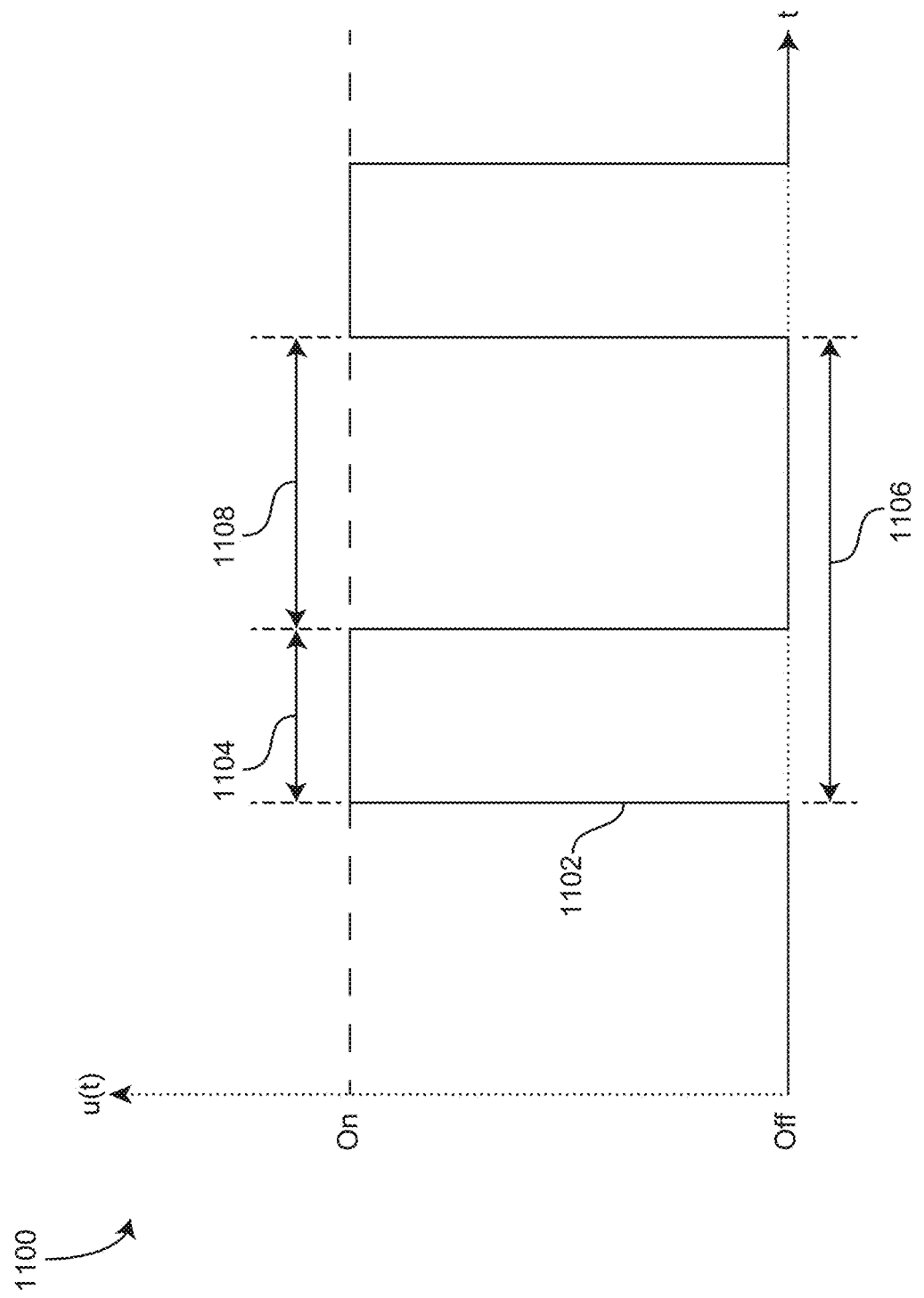
FIG. 11 is an illustrative graph of a duty cycle of a pump of the NPWT device of FIG. 1, according to an exemplary embodiment.

Referring now to FIG. 11, an illustrative graph 1100 of a duty cycle resulting from PWM is shown, according to some embodiments. In some embodiments, controller 110 include a PWM manager, configured to use PWM to adjust an operation of pump 142. In some embodiments, the PWM manager is the pump manager as described in greater detail above with reference to FIG. 2. The illustrative graph 1100 is shown to include a series 1102 actuating between an on state and an off state, according to some embodiments. The y-axis of graph 1100 represents the on state and the off state of a controlled equipment (e.g., pump 142), and the x-axis of graph 1100 represents time (e.g., time increasing), according to some embodiments. In some embodiments, series 1102 is shown being in the on state for time interval 1104, and in the off state for time interval 1108. In some embodiments, time interval 1104 is referred to as a pulse width PW. The summation of time interval 1104 and time interval 1108 is defined as period 1106 (T), according to some embodiments. In some embodiments, the duty cycle is determined using a duty cycle equation, mathematically represented as $D=PW/T\times 100\%$. In the duty cycle equation shown, D is the duty cycle (in terms of %), PW is time interval 1104, and T is period 1106, according to some embodiments. In this way, the duty cycle relates the on-time with the off-time, indicating an amount of time the controlled equipment has been in the on-state with respect to period 1106. When applied to pumps, duty cycle is a total amount of time the pump is in the on-state over an hour of operation, according to some embodiments. Controller 110 is configured to modulate the pulse width PW (i.e., time interval 1104) to achieve various therapy pressure setpoints, according to some embodiments.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:

1. A method for dynamically controlling an alarm of a negative pressure wound therapy (NPWT) device, the method comprising:
   initiating NPWT;
   comparing an initial pump duty to a threshold value to determine a dressing application quality;
   monitoring a leakage rate of the NPWT;
   setting a leak threshold value based on the dressing application quality;
   determining a plurality of leakage event occurrences in response to the leakage rate exceeding the leak threshold value at a plurality of times;
   adjusting the leak threshold value based on at least one of a number of the plurality of leakage events over the time period, a time duration between sequentially occurring leakage events of the plurality of leakage events, and the dressing application quality; and
   causing a user interface device to display a leak alert in response to the leakage rate exceeding the adjusted leak threshold value.

2. The method of claim 1, wherein initiating NPWT comprises increasing a vacuum pressure to draw down and seal a dressing for NPWT.

3. The method of claim 1, wherein determining the dressing application quality comprises characterizing the dressing application as a low leak rate application in response to the initial pump duty being less than the threshold value and characterizing the dressing application as a high leak rate application in response to the initial pump duty being greater than the threshold value.

4. The method of claim 1, further comprising receiving signals from an accelerometer to detect motion of the NPWT device.

5. The method of claim 4, further comprising adjusting the leak threshold value based on the detected motion of the NPWT device.

6. The method of claim 1, further comprising receiving location information from at least one of a GPS and a user device and adjusting the leak threshold value based on the received location.

7. The method of claim 1, further comprising receiving information from a light sensor, the information from the light sensor indicating an intensity of light at the NPWT device, and adjusting the leak threshold value based on the indicated light intensity.

8. The method of claim 1, further comprising receiving information regarding a state of charge or a remaining amount of energy of an energy storage device configured to provide the NPWT device with power, and adjusting the leak threshold value based on the information regarding the state of charge or the remaining amount of energy of the energy storage device.

9. The method of claim 1, further comprising increasing an amount of time between sequentially occurring leak alerts based on at least one of the number of the plurality of leakage events over the time period, and the dressing application quality.

10. A controller for providing leak alerts for a Negative Pressure Wound Therapy (NPWT) device, the controller configured to:
    determine an initial seal quality by comparing an initial pump duty value to a pump duty threshold value;
    monitor a leak rate of a NPWT seal;
    determine a plurality of leak events in response to the leak rate exceeding a predetermined leak rate threshold value at a plurality of times over a time period;
    determine a number of the plurality of leak events over the time period;
    provide an alert in response to the leak rate exceeding the predetermined leak rate threshold;
    adjust at least one of the predetermined leak rate threshold value and a time between alerts based on at least one of the initial seal quality and the number of the plurality of leak events over the time period.

11. The controller of claim 10, further configured to adjust at least one of the leak rate threshold value and the time between alerts based on at least one of a location of the NPWT device, a detection of motion of the NPWT device, and an amount of remaining battery life of the NPWT device.

* * * * *